US008533008B2

(12) United States Patent
Kahn et al.

(10) Patent No.: US 8,533,008 B2
(45) Date of Patent: Sep. 10, 2013

(54) CLINICAL TRIALS MANAGEMENT SYSTEM AND METHOD

(75) Inventors: Michael G. Kahn, Boulder, CO (US); Michael Mischke-Reeds, San Francisco, CA (US)

(73) Assignee: Medidata Solutions, Inc., New York, NY (US)

( * ) Notice: Subject to any disclaimer, the term of this patent is extended or adjusted under 35 U.S.C. 154(b) by 392 days.

(21) Appl. No.: 12/505,860

(22) Filed: Jul. 20, 2009

(65) Prior Publication Data

US 2009/0313048 A1  Dec. 17, 2009

Related U.S. Application Data

(63) Continuation of application No. 09/584,936, filed on May 31, 2000, now abandoned.

(51) Int. Cl.
*G06Q 50/00* (2012.01)
(52) U.S. Cl.
USPC .................................. 705/3; 705/2; 705/7.27
(58) Field of Classification Search
USPC ................................................ 705/3, 7.27, 2
See application file for complete search history.

(56) References Cited

U.S. PATENT DOCUMENTS

| | | |
|---|---|---|
| 4,992,939 A | 2/1991 | Tyler |
| 5,148,366 A | 9/1992 | Buchanan et al. |
| 5,181,162 A | 1/1993 | Smith et al. |
| 5,222,236 A | 6/1993 | Potash et al. |
| 5,267,155 A | 11/1993 | Buchanan et al. |
| 5,272,623 A | 12/1993 | Grubb et al. |
| 5,369,763 A | 11/1994 | Biles |
| 5,553,216 A | 9/1996 | Yoshioka et al. |
| 5,655,130 A | 8/1997 | Dodge et al. |
| 5,657,255 A | 8/1997 | Fink et al. |
| 5,666,490 A | 9/1997 | Gillings et al. |
| 5,734,883 A | 3/1998 | Umen et al. |
| 5,774,887 A | 6/1998 | Wolff et al. |

(Continued)

FOREIGN PATENT DOCUMENTS

| | | |
|---|---|---|
| CA | 2150765 | 7/2000 |
| EP | 0 832 462 | 8/2002 |

(Continued)

OTHER PUBLICATIONS

"Instruction," Merriam-Webster Online Dictionary, Merriam-Webster Online, http://www.merriam-webster.com/dictionary/instruction (last visited Sep. 25, 2009).

(Continued)

*Primary Examiner* — Lena Najarian
(74) *Attorney, Agent, or Firm* — Hoffmann & Baron, LLP

(57) ABSTRACT

Meta-models are made available to clinical trial protocol designers. A meta-model includes a list of preliminary patient eligibility attributes appropriate for a particular disease category. The protocol designer chooses the appropriate meta-model, and encodes the clinical trial protocol, including eligibility and patient workflow, within the selected meta-model in a protocol database. The resulting protocol database is stored together with databases of other protocols in a library of protocol databases. Sponsors and individual clinical sites have controlled access to the protocols. Study sites make reference to the protocol database in order to perform patient eligibility screening. Once a patient is enrolled into a study, the protocol database indicates to the clinician what workflow tasks are to be performed at each patient visit.

17 Claims, 26 Drawing Sheets

(56) References Cited

U.S. PATENT DOCUMENTS

| | | | |
|---|---|---|---|
| 5,812,983 | A | 9/1998 | Kumagai |
| 5,812,984 | A | 9/1998 | Goltra |
| 5,832,449 | A | 11/1998 | Cunningham |
| 5,867,821 | A | 2/1999 | Ballantyne et al. |
| 5,898,586 | A | 4/1999 | Jeatran et al. |
| 5,930,799 | A | 7/1999 | Tamano et al. |
| 5,963,967 | A | 10/1999 | Umen et al. |
| 5,991,731 | A | 11/1999 | Colon et al. |
| 6,000,828 | A * | 12/1999 | Leet .................................. 705/2 |
| 6,018,713 | A | 1/2000 | Coli et al. |
| 6,055,494 | A | 4/2000 | Friedman |
| 6,081,786 | A | 6/2000 | Barry et al. |
| 6,081,809 | A | 6/2000 | Kumagai |
| 6,108,635 | A | 8/2000 | Herren et al. |
| 6,196,970 | B1 | 3/2001 | Brown |
| 6,205,455 | B1 | 3/2001 | Umen et al. |
| 6,505,218 | B2 | 1/2003 | Umen et al. |
| 6,519,601 | B1 * | 2/2003 | Bosch .................................. 1/1 |
| 6,687,190 | B2 | 2/2004 | Momich et al. |
| 6,839,678 | B1 | 1/2005 | Schmidt et al. |
| 7,054,823 | B1 * | 5/2006 | Briegs et al. ....................... 705/2 |
| 7,251,609 | B1 | 7/2007 | McAlindon et al. |
| 2001/0051882 | A1 | 12/2001 | Murphy et al. |
| 2002/0016530 | A1 | 2/2002 | Brown |

FOREIGN PATENT DOCUMENTS

| | | |
|---|---|---|
| EP | 1 244 024 | 9/2002 |
| WO | WO 96/34348 | 10/1996 |
| WO | WO 98/49657 | 11/1998 |
| WO | WO 99/63473 | 12/1999 |

OTHER PUBLICATIONS

21 C.F.R Ch. 1, Part II, "Electronic Records; Electronic Signatures" (Apr. 1, 1999).
Advani et al., "Domain Modeling with Integrated Ontologies: Principles for Reconciliation and Reuse." SMI Report No. SMI-97-0681 (1997).
Anonymous, "Documentum Market Application Profile" (advertisement), Documentum Inc. (no date).
Anonymous, "Accurate Information & Ontos." Release 1.0, vol. 91, No. 7, A Monthly Report by Esther Dyson, pp. 23-24 (Jul. 31, 1991).
Anonymous, "Black and Veatch selects Documentum as corporate document management standard; largest U.S. engineering and design firm implements Documentum to increase competitive advantage in worldwide market," Business Wire. pp. 12061100, Dec. 6, 1994, Gale Group, http://www.thefreelibrary.com/_/print/PrintArticle.aspx?id=15947136 (last visited Sep. 17, 2009).
Anonymous, "Clinical Trials: Eliminating the Paper Chase," In Vivo: The Business & Medicine Report, p. 47; http://www.windhover.com/contents/montly/exe/e (Dec. 1999).
Anonymous, "Drkoop.com and Quintiles Launch service to Recruit Clinical Trial Patients on the Internet," PR Newswire, (Jun. 28, 1999).
Anonymous, SGML.Primer. "What Every Software Company Should Know about SGML," Release 1.0, vol. 91, No. 7: A Monthly Report by Esther Dyson (Jul. 31, 1991).
Anonymous, "The ICP (Intelligent Clinical Protocol) Is A Sophisticated, Computer-Based Model Of A Clinical Protocol That Fully Encompasses The Trial's Clinical and Operational Aspects," Fast Track System, Inc. Offices (2001).
Anonymous, "Universal Systems Inc. Launches Updates Version of e.Power Clinical CRF WorkManager to Accelerate Clinical Trials and Facilitate Global Processing," PR Newswire (Jun. 28, 1999).
Anonymous, "Versal Technologies, Inc. Announces versal Web Trial (T.M.) Version 2.0 A Web-Based Data Management System for Clinical Trials, " PR Newswire (Mar. 31, 1999), http://proquest.umi.com/pqdweb?Did= (last visited Jul. 11, 2003).
Anonymous, Centerwatch.com, "Glossary," available http:/www.centerwatch.com/patient/glossary.html (last visited Dec. 8, 2003).
Breitfeld et al., "Pilot Study of a Point-of-use Decision Support Tool for Cancer Clinical Trials Eligibility," JAMIA, vol. 6, No. 6: pp. 466-477 (Nov./Dec. 1999).
Brenesal, B., "Q & A 4.0: the tradition continues," P.C. Sources, vol. 2, No. 10: pp. 361 (Oct. 1991).
Broverman, Carol A. "Overview of Controlled Clinical Terminologies," slides for CME Course (Aug. 18, 1999).
Brown, Stephen J., U.S. Appl. No. 09/201,323, filed Nov. 30, 1998, entitled Leveraging Interaction with a Community of Individuals.
CancerNet Clinical Trials Search, p. 1 of 2, available at http://cancernet.nci.nih.aov/trialsrch.shtml, with Search Narrowing p. 1 of 2, and with Search Results p. 1 of 8, and with "Phase I Pilot Study of Oxaliplation in Combination With Capecitabine in Patients With Solid Tumors." Protocol IDs NCI-99-C0117, NCI-T99-0011, and MB-NAVY-99-01, pp. 1-4, available at http://cancernet.nci.nih.gov/cgi-bin/srchcgi.exe?TYPE=search&DBID=allprotocol&ZUI=199_14398&PASSTHRU=%3aip%3a207%2e235%2e14%3a%aprof%3aip:207.88.235.14:prof::recno:1:&SFMT=prot_summary/1/0/0 (last visited Apr. 1, 2000).
Carlson et al., "Computer-Based Screening of Patients with HIV/AIDS for Clinical-Trial Eligibility," Online Journal of Current Clinical Trials: Knowledge Systems Laboratory Report KSL-95-59 (Mar. 1995).
Carlson et al., "Potential Accrual of Patients to Prospective Clinical Trials," Stanford University, ,Knowledge System Laboratory, Report No. KSL⁻93-28 (Jun. 1993).
Cimino, J.J., "Desiderata for Controlled Medical Vocabularies in the Twenty-First Century," Methods of Information in Medicine: vol. 37: pp. 394-403 (1998).
Cimino, J.J., "Distributed cognition and knowledge-based controlled medical terminologies," Artificial Intelligence in Medicine, vol. 12: pp. 153-168 (Feb. 98).
Cimino, J.J., "Editorial: The Concepts of Language and the Language of Concepts," Methods of Information Medicine: vol. 37: p. 311 (1998).
DataEdge LLC., "Indexes of Clinical Trial Costs Per Patient, 1993-1999," In: Mathieu MP, Editor Parexel's Pharmaceutical R&D Statistical Sourcebook 2000, Waltham, MA: Parexel International Corp, p. 67 (2000).
DataEdge LLC.,"Indexes of Clinical Study Complexity, 1993-1999," In: Mathieu MP, Editor Parexel's Pharmaceutical R&D Statistical Sourcebook 2000, Waltham, MA: Parexel International Corp: pp. 66 (2000).
Domain Pharma Corporation, "Clinical 4," Release 4.2 (Brochure) (1999).
Domain Pharma, "Clintrial 4," Reference Guide, Release 4,2, pp. 1-380 (1999).
Domain Pharma, "Clintrial 4," Entering, Editing and Retrieving Data, Release 4,2, pp. 1-366 (1999).
Domain Pharma, "Clintrial 4," Managing Data, Release 4.2, pp. 1-352 (1999).
Domain Pharma, "Clintrial 4," Setting Tip Clintrial, Release 4.2, pp. 1-478 (1999).
Domain Pharma, "Clintrial 4," Working with Review, Release 4.2, pp. 1-532 (1999).
Domain Pharma, "Clintrial 4," working with Multisite, Release 4.2, pp. 1-204 (1999).
Domain Pharma, Clintrial Database Schema, Version 4.2 (Modified Nov. 6, 1998).
Dvorin, Jeffrey, "Clinical Trials: Eliminating the Paper Chase," In Vivo: The Business and Medicine Report: pp. 1-9, http://www.windhoverinfo.com (last visited Dec. 1999).
Dyson, Esther, "SFQL: When Structure Counts," Release 1.0, http://findarticles.com/p/articles/mI_m0REL/is_n4_v91/ai_10757335/ (last visited Sep. 17, 2009).
Fan et al., "Unitized Data System: A new Formalism for Encoding and Presenting Data From The Scientific Research Literature, " J. of the Amer. Soc. for Info. Science, vol. 45, No. 5: pp. 371-383 (1992).
FDA, "Guidance for Industry: Computerized Systems Used in Clinical Trials" (Apr. 1999).
FDA, "Guidance for Industry E6 Good Clinical Practice: Consolidated Guidance," ICH, http://www.fda.gov/downloads/regulatoryinformation/guidances/UCM129515.pdf (Apr. 1996).

Fridsma, Douglas B. et al., "Representing Medical Protocols for Organizational Simulation: An Information Processing Approach," Computational & Mathematical Org. Theory, vol. 4 No. 1: pp. 71-95 (1998).

Grosso et al., "Knowledge Modeling at the Millennium (The Design and Evolution of Protege—2000)," SMI Report No. SMI-1999-0801 (1999), available at http://smi-web.stanford.edu/pubs/SMIAbstracts/SMI-1999-0801.html (last visited on Jan. 1, 2000).

Hampshire, N., "dbPublisher," EXE 4(4) pp. 24 et. seq (Sep. 1989).

Holford et al., "Simulation of Clinical Trials," Annu. Rev. Pharmacol. Toxicol, vol. 40: pp. 209-234 (2000).

ICH Expert Working Group, "ICH Harmonised Tripartite Guideline: General Considerations for Clinical Trials." International Conference on Harmonisation of Technical Requirements for Registration of Pharmaceuticals for Human Use recommended for adoption on Jul. 17, 1997, URL: www.ifpma.orglich5e.html (last visited Aug. 31, 2001).

ICH Expert Working Group, "ICH Harmonised Tripartite Guideline: Guideline for Good Clinical Practice," International Conference on Harmonisation of Technical Requirements for Regisrtation of Pharmaceuticals for Human Use recommended for Adoption on May 1, 1996, URL:www.ifphma.org/ich5e.html, (last visited Aug. 31, 2001).

iKnowMed, Physician Solutions, web page screen shorts available at http://www.knowmed.com/solutions_advanced.html (last visited Apr. 20, 2000).

Ingenerf, J. and Giere, W. "Concept-Oriented Standardization and Statistics-Oriented Classification: Continuing the Classification versus Nomenclature Controversy," Methods of Information in Medicine, vol. 37: pp. 527-539 (1998).

Kitney R I et al. "Clinical trials of an electronic medical record system," Computers in Cardiology 1998 Cleveland, LH, USA Sep. 13-16, 1998, New York, NY, USA IEEE, US, Sep. 13, 1998, pp. 201-204, XP010314371 ISBN: 0-7803-5200-9.

Kroll J. A et al., "Study Conduct Delays are Getting Worse." In: Kroll IA, editor, An Industry In Evolution, Second ed., Boston, MA: CenterWatch, p. 99 (1999).

Kuhn et al., "Now Securing Every Row," Oracle Magazine (Jul./Aug. 2003).

L Ohno-Machado et al., "Decision Support for Clinical Trial Eligibility Determination In Breast Cancer," Proc. AMIA Symp. (1999).

L. Ohno-Machado et al., "AIDS2: A Decision-Support Tool for Decreasing Physicians' Uncertainty Regarding Patient Eligibility for HIV Treatment Protocols," Proc. Annu. Symp. Comput. Appl. Med. Care, pp. 429-433 (1993).

MA Musen, SW Tu, AK Das, Y Shahar, "EON: A component-based approach to automation of protocol-directed therapy," J. Am. Med. Inform. Assoc. (1996).

Manell, Per.. "Pharmaceutical Document Management," (Presentation Slides), PharmaSoft AB (Feb. 12-15, 1995).

Man, Andrew P., "SGML—The Business Perspective," (Presentation Slides) Glaxo Research & Development Ltd. (Feb. 12-15, 1995).

Matoren, Gary M., "The Clinical Research Process in the Pharmaceutical Industry," New York: Marcel Dekker, Inc., Chapters 8, 9, and 11 (1984).

Mori et al., "Standards to Support Development of Terminological Systems for Health Care Telematics," Methods of Information in Medicine: vol. 37: pp. 551-563 (1998).

Musen et al., "EON: A Component-Based Approach to Automation of Protocol-Directed Therapy," SMI Report No. SMI-96-0606, JAMIA 3:367-388 (1996).

Musen et al., "Protégé-11: Computer Support for Development of Intelligent Systems from Libraries of Components," MEDINFO 95 Proceedings. R.A. Greens et al. (editors), vol. 8, No. 1: pp. 766-770.

Musen, Mark A., "Domain Ontologies in Software Engineering: Use of Protege with the EON Architecture," Methods of Information in Medicine vol. 37: pp. 540-550, SMI Report No. SMI-97-0657 (1998).

Musen.et al., "Knowledge Engineering for a Clinical Trial Advice System: Uncovering Errors in Protocol Specification," Report KSL-85-51, Proceedings AAMSI Congress 1986 (Levy, A.H. and Williams, B.T., eds.), pp. 24-27, Anaheim CA (May 1986).

Ohno-Machado et al., "Decision Support for Clinical Trial Eligibility Determination in Breast Cancer," Proc. AMIA Symp., pp. 340-344 (1999).

Ohno-Machado et al., "The GuideLine Interchange Format: A Model for Representing Guidelines," Journal of the American Medical Informatics Association, vol. 5 No. 4: pp. 357-372 (Jul.-Aug. 1998).

Pallatto, J., "Software design tool gets new module," PC Week, vol. 5, No. 41, p. 24, (Oct. 10, 1988).

Phase Forward, Incorporated, "Products Overview," web page, available at http://hvww.phaseforward.com/prodcuts/products.htm (Last Visited Apr. 26, 2000).

Rubin et al., "Tool Support for Authoring Eligibility Criteria for Cancer Trials," Smith Report No. SMI-99-0779 (1999).

Schettini et al., "SGML is Here to Stay. Coding Documents with Standard Generalized Markup Language Lets You Manipulate and Format Text in Limitless Ways," vol. 9, No. 6, pp. 71-78 (Jun. 1994).

Schmuff, Norman R., "The Standards—Based CMC CANDA Project—Background." (presentation slides), Food and Drug Administration. (Feb. 14-15, 1994).

Seymour, J., "Forms Software; Next Hot Category," PC Magazine, vol. 7, No. 16, pp. 77(2) (Sep. 1988).

Sheiner et al., "Pharmacokinetic/Pharmacodynamic Modeling in Drug Device Development," Annu. Rev. Pharmacol Toxicol., vol. 40: pp. 67-95, Annual Reviews (2000).

Spiker, Bert., "Guide to Clinical Trials," Chapter 2 pp. 7-9; Chapter 3 pp. 10-14; Chapter 4 pp. 15-20; Chapter 5 pp. 21-26; Chapter-12:pp. 78-84; Chapter 68 pp. 482-489; Chapter 122, pp. 953-960, Lippincott Williams & Wilkins (1991).

Tu et al., "A Methodology for Determining Patients' Eligibility for Clinical Trials," Methods of Information in Medicine, No. 32, pp. 317-325 (1993).

U.S. Appl. No. 60/131,528, filed Apr. 29, 1999, "Method for Conducting Clinical Trials Entirely Over the Internet," Dr. Timothy E. McAlindon.

Walter, M. "Documentum: open approach to automating, workflow and management of long documents,"Seybold Report of Publishing Systems, vol. 23 No. 7, pp. 3(11) (Dec. 1, 1993).

Wampler Suzanne, "Tackling Protocol Complexity," Good Clinical Practice Journal, vol. 7, No. 2: pp. 6-8 (2000).

Woollen, Stan W.,"Computerized Systems Used in Clinical Trials," Slides for ACRP Annual Meeting (May 27, 1999).

* cited by examiner

FIG. 2 cancer_protocols_INSTANCE_00039 (instance of Cancer_Clinical_Protocol)

| Label |
|---|
| CALGB 49802 |

Title
Phase III Study of Adriamycin/Taxotere vs Adriamycin/Cytoxan for the Adjuvant treatment of Node Positive or High Risk Node Negative Breast Cancer

Clinical Algorithm
CALGB 49802 Level 1

Context Reference

Version
mgk 25Jan00

Authors
M.G. Public

Authors
◇ MUSC PRN web page

Entry Criteria (1 values)

Protocol Name
CALGB 49802

Clinical State Name

◇ Histologically or cytologically confirmed invasive breast cancer
◇ 1-3 histologically involved axillary lymph nodes
◇ No evidence of metastatic disease (M0)
◇ Absolute neutrophil count at least 1,500/mm3
◇ Platelet count at least 100,000/mm3
◇ Left ventricular rejection fraction at rest at least 45% by MUGA
◇ Bilirubin no greater than 1.2 times upper limit of normal (ULN)
◇ Age 18-70
◇ Effective contraception required of fertile women        210
◇ No prior chemotherapy
◇ No prior radiotherapy
◇ No concurrent estrogen therapy

Exclusion List
◇ Tumor of any size with direct extension to chest wall or skin (T4)        212
◇ Patient is pregnant or nursing

FIG. 12

```
FastTrack Protocol_INSTANCE_00212 (instance of Portocol)    — ☐ ✕
ProtocolTitle
A Phase III Study of Paclitaxel via Weekly 1-Hour Infusion
ProtocolIdentifier
CALGB 49802
OfficalSourceDocument
http://prn.musc.edu/research/protocol/deptmed/divhoc/br
ShortDescription
CALGB 49802
StudyChair
Andrew D. Seidman, M.D.
Sponsor
CALGB
QuickScreenCriterion                                  ▷
Breast Cancer
ProtocolObjectives                                ◁ ☐ ▷
To compare "standard" (S) paclitaxel at 175 mg/m2 via
3-hour infusion every 3 weeks to "dose-dense" (DD)
paclitaxel at 80 mg/m2 via 1-hour infusion every week
TrialStatus              AccrualStatus
Active            ▷     Open for accrual    ▷
TrialPhase               TrialType
Phase III         ▷     Cooperative-group   ▷

Version
Update #1
VersionDate
December 15, 1998
EligibilityCriteriaSet                    V C + −
◇ CALGB 9840 Eligibility Criteria  ← 1212

LongDescription

FirstVisit                                V C + −
Screening Visit
ProtocolSchemaDiagram                     V C + −
CALGB 9840 Schema                       ← 1214
```

1210 points to ProtocolObjectives field.

FIG. 20

FastTrack Protocol_INSTANCE_00206 (instance of ManagementTask)

ShortDescription

Give Arm A Paclitaxel Treatment

LongDescription

Give Paclitaxel 175mg/m2 2 IV, 3 hours. This treatment is given to patients in Arm A of the CALGB 9840 protocol. It is given once every 3 weeks. One cycle is equivalent to one infusion. Granulocyte count must be >= 1500/ul and platelet count must be >= 100,00/ul on day 1 of each cycle in order to proceed with the Paclitaxel infusion. Patient must receive the pre-medication prior to Paclitaxel infusion. If either the granulocyte or platelet count are not adequate, do not continue with treatment. Patients should receive a minimum of cycle unless there is rapid disease progression.
Expected toxicities:
The dose-limiting toxicity of Paclitaxel is neutropenia. Other known toxicities include nausea and vomiting, diarrhea, stomatitis, mucositis, pharyngitis, typhlitis, ischemic colitis, brandycardia, atrial arrhythmia, hypotension, hypertension, sensory (taste), peripheral neuropathy, seizures, mood, hepatic encephalopathy, acute anaphylactic and urticarial reactions, flushing, rash, pruritis, increased SGOT, SGPT, bilirubin and/or alkaline phosphatase, hepatic failure, hepatic necrosis, alopecia, fatigue, arthralgia, myalgia,light-headedness, myophathy, visual changes (sensation of flashing lights, blurred vision). Local infiltration with Paclitaxel will cause mild local symptoms (erytherma, discomfort, induration) that usually resolve within a week. If infiltration occurs, there is the rare possibility of ulceration or rash. Seizure have been reported rarely in association with Paclitaxel use.
Dose Modifications:
Allergic Reactions: Patients with grade 1 or 2 allergic reactions may have treatment continued without modifications. Patient with grade 3 or 4 allergic reactions who are resounding to treatment may remain on protocol therapy after discussion with Study Chair. Such patients are at risk for recurrent allergic reactions. As a first maneuver, treatment after premedication with oral recurrent allergic reactions. As a first maneuver retreatment after premedication with oral dexamethasone 20 mg at 12 and 6 hours pre-administration of Paclitaxel, along with IV H1 and h2-=receptor antagonist should be attempted. If necessary, thereafter, infusion rate adjustments will be considered and additional premedications will be administered. These must be informed of the potential risks of recurrent allergic reactions and must be carefully monitored.
Hematologic Toxicity: Patients are managed as clinically indicated. Colony stimulation factors (GCSF) should be used in the manner described below. Exceptions should be discussed with the study chair

SiteLongDescription

*FIG. 21*

```
FastTrack Protocol_INSTANCE_00196 (instance of ManagementTask)
ShortDescription
[ Submit Form C-116 ]

LongDescription
[ Submit CALGB Advanced Breast Cancer Followup-form (C-116) every two
  cycles while on protocol therapy, at 6 & 12 months after end of
  treatment, at disease progression or initiation of non-protocol therapy. ]

SiteLongDescription
[ ]
SiteShortDescription
[ ]
```

FIG. 23

FastTrack Protocol_INSTANCE_00014 (instance of VisitToVisitTransition)

ShortDescription
Arm A Treatment Arm A treatment Retry #

PreferredRelativeTime
7

First Object
Arm A Treatment Visit

MaximumRelativeTime
7

Second Object
Arm A Treatment Retry #1

MinimumRelativeTime
7

LongDescription
If either granulocte or platelet count are not adequate, blood count should be repeated weekly and treatment should be instituted when there has been hematologic recovery. Patients receiving G-CSF are not eligible for re-treatment unless they have been off G-CSF for a minimum of 24 hours.

SiteLongDescription

SiteShortDescription

1818

CLINICAL TRIALS MANAGEMENT SYSTEM AND METHOD

CROSS-REFERENCE TO RELATED APPLICATIONS

This application is a continuation of U.S. application Ser. No. 09/584,936, filed May 31, 2000, now pending.

BACKGROUND

1. Field of the Invention

The invention relates to the field of medical informatics, and more particularly to a system and method using medical informatics primarily to plan, conduct and analyze clinical trials and their results.

2. Description of Related Art

Over the past number of years, the pharmaceutical industry has enjoyed great economic success. The future, however, looks more challenging. During the next few years, products representing a large percentage of gross revenues will come off patent, increasing the industry's dependence upon new drugs. But even with new drugs, with different companies using the same development tools and pursuing similar targets, first-in-category market exclusivity has also fallen dramatically. Thus in order to compete effectively in the future, the pharmaceutical industry needs to increase throughput in clinical development substantially. And this must be done much faster than it has in the past—time to market is often the most important factor driving pharmaceutical profitability.

A. Clinical Trials: the Now and Future Bottleneck

In U.S. pharmaceutical companies alone, a huge percentage of total annual pharmaceutical research and development funds is spent on human clinical trials. Spending on clinical trials is growing at approximately 15% per year, almost 50% above the industry's sales growth rate. Trials are growing both in number and complexity. For example, the average new drug submission to the U.S. Food & Drug Administration (FDA) now contains more than double the number of clinical trials, more than triple the number of patients, and a more than a 50% increase in the number of procedures per trial, since the early 1980s.

An analysis of the new drug development process shows a major change in the drivers of time and cost. The discovery process, which formerly dominated time to market, has undergone a revolution due to techniques such as combinatorial chemistry and high-throughput screening. The regulatory phase has been reduced due to FDA reforms and European Union harmonization. In their place, human clinical trials have become the main bottleneck. The time required for clinical trials now approaches 50% of the 15 years or so required for the average new drug to come to market.

B. The Trial Process Today

The conduct of clinical trials has changed remarkably little since trials were first performed in the 1940's. Clinical research remains largely a manual, labor-intensive, paper based process reliant on a cottage industry of physicians in office practices and academic medical centers.

1. Initiation

A typical clinical trial begins with the construction of a clinical protocol, a document which describes how a trial is to be performed, what data elements are to be collected, and what medical conditions need to be reported immediately to the pharmaceutical sponsor and the FDA. The clinical protocol and its author are the ultimate authority on every aspect of the conduct of the clinical trial. This document is the basis for every action performed by multiple players in diverse locations during the entire conduct of the trial. Any deviations from the protocol specifications, no matter how well intentioned, threaten the viability of the data and its usefulness for an FDA submission.

The clinical protocol generally starts with a cut-and-paste word-processor approach by a medical director who rarely has developed more than 1-2 drugs from first clinical trial to final regulatory approval and who cannot reference any historical trials database from within his or her own company—let alone across companies. In addition, this physician typically does not have reliable data about how the inclusion or exclusion criteria, the clinical parameters that determine whether a given individual may participate in a clinical trial, will affect the number of patients eligible for the study.

A pharmaceutical research staff member typically translates portions of the trial protocol into a Case Report Form (CRF) manually using word-processor technology and personal experience with a limited number of previous trials. The combined cutting and pasting in both protocol and CRF development often results in redundant items or even irrelevant items being carried over from trial to trial. Data managers typically design and build database structures manually to capture the expected results. When the protocol is amended due to changes in FDA regulations, low accrual rates, or changing practices, as often occurs several times over the multiple years of a big trial, all of these steps are typically repeated manually.

At the trial site, which is often a physician's office, each step of the process from screening patients to matching the protocol criteria, through administering the required diagnostics and therapeutics, to collecting the data both internally and from outside labs, is usually done manually by individuals with another primary job (doctors and nurses seeing 'routine patients') and using paper based systems. The result is that patients who are eligible for a trial often are not recruited or enrolled, errors in following the trial protocol occur, and patient data are often either not captured at all, or are incorrectly transcribed to the CRF from hand written medical records, and are illegible. An extremely large percentage of the cost of a trial is consumed with data audit tasks such as resolving missing data, reconciling inconsistent data, data entry and validation. All of these tasks must be completed before the database can be "locked," statistical analysis can be performed and submission reports can be created.

2. Implementation

Once the trial is underway, data begins flowing back from multiple sites typically on paper forms. These forms routinely contain errors in copying data from source documents to CRFs.

Even without transcription errors, the current model of retrospective data collection is severely flawed. It requires busy investigators conducting multiple trials to correctly remember and apply the detailed rules of every protocol. By the time a clinical coordinator fills out the case report form the patient is usually gone, meaning that any data that was not collected or treatment protocol complexities that were not followed are generally unrecoverable. This occurs whether the case report form is paper-based or electronic. The only solution to this problem is point-of-care data capture, which historically has been impractical due to technology limitations.

Once the protocol is in place it often has to be amended. Reasons for changing the protocol include new FDA guidelines, amended dosing rules, and eligibility criteria that are found to be so restrictive that it is not possible to enroll enough patients in the trial. These "accrual delays" are among the most costly and time-consuming problems in clinical trials.

The protocol amendment process is extremely labor intensive. Further, since protocol amendments are implemented at different sites at different times, sponsors often don't know which protocol is running where. This leads to additional 'noise' in the resulting data and downstream audit problems. In the worst case, patients responding to an experimental drug may not be counted as responders due to protocol violations, but even count against the response rate under an intent-to-treat analysis. It is even conceivable that this purely statistical requirement could cause an otherwise useful drug to fail its trials.

Sponsors, or Contract Research Organizations (CROs) working on behalf of sponsors, send out armies of auditors to check the paper CRFs against the paper source documents. Many of the errors they find are simple transcription errors in manually copying data from one paper to the other. Other errors, such as missing data or protocol violations, are more serious and often unrecoverable.

3. Monitoring

The monitoring and audit functions are one of the most dysfunctional parts of the trial process. They consume huge amounts of labor costs, disrupt operations at trial sites, contribute to high turnover, and often involve locking the door after the horse has bolted.

4. Reporting

As information flows back from sites, the mountain of paper grows. The typical New Drug Application (NDA) literally fills a semi-truck with paper. The major advance in the past few years has the addition of electronic filing, but this is basically a series of electronic page copies of the same paper documents—it does not necessarily provide quantitative data tables or other tools to automate analysis.

B. The Costs of Inefficiency

It can be seen that this complex manual process is highly inefficient and slow. And since each trial is largely a custom enterprise, the same thing happens all over again with the next trial. Turnover in the trials industry is also high, so valuable experience from trial to trial and drug to drug is often lost.

The net result of this complex, manual process is that despite accumulated experience, it is costing more to conduct each successive trial.

In addition to being slow and expensive, the current clinical trial process often hurts the market value of the resulting drug in two important ways. First, the FDA reviews drugs on an "intent to treat" basis. That means that every patient enrolled in a trial is included in the denominator (positive responders/total treated) when calculating a drug's efficacy. However, only patients who respond to treatment and comply with the protocol are included in the numerator as positive responders. Not infrequently, a patient responds to a drug favorably, but is actually counted as a failure due to significant protocol non-compliance. In rare cases, an entire trial site is disqualified due to non-compliance. Non-compliance is often a result of preventable errors in patient management.

The second major way that the current clinical trail process hurts drug market value is that much of the fine grain detail about the drug and how it is used is not captured and passed from clinical development to marketing within a pharmaceutical company. As a result, virtually every pharmaceutical company has a second medical department that is a part of the marketing group. This group often repeats studies similar to those used for regulatory approval in order to capture the information necessary to market the drug effectively.

C. The Situation at Trial Sites

Despite the existence of a large number of clinical trials that are actively recruiting patients, only a tiny percentage of eligible patients are enrolled any clinical trial. Physicians, too, seem reluctant to engage in clinical trials. One study by the American Society of Clinical Oncology found that barriers to increased enrollment included restrictive eligibility criteria, large amount of required paperwork, insufficient support staff, and lack of sufficient time for clinical research.

Clinical trials consist of a complex sequence of steps. On average, a clinical trial requires more than 10 sites, enrolls more than 10 patients per site and contains more than 50 pages for each patient's case report form (data entry sheet). Given this complexity, delays are a frequent occurrence. A delay in any one step, especially in early steps such as patient accrual, propagates and magnifies that delay downstream in the sequence.

A significant barrier to accurate accrual planning is the difficulty trial site investigators have in predicting their rate of enrollment until after a trial as begun. Even experienced investigators tend to overestimate the total number of enrolled patients they could obtain by the end of the study. Novice investigators tend to overestimate recruitment potential by a larger margin than do experienced investigators, and with the rapid increase in the number of investigators participating in clinical trials, the vast majority of current investigators have not had significant experience in clinical trials.

D. Absence of Information Infrastructure

Given the above state of affairs, one might expect that the clinical trials industry would be ripe for automation. But despite the desperate need for automation, remarkably little has been done.

While the pharmaceutical industry spends hundreds of millions of dollars annually on clinical information systems, most of this investment is in internal custom databases and systems within the pharmaceutical company; very little of this technology investment is at the physician office level. Each trial, even when conducted by the same company or when testing the same drug, is usually a custom collection of sites, procedures and protocols. More than half of trials are conducted for the pharmaceutical industry by Contract Research Organizations (CROs) using the same manual systems and custom physician networks.

The clinical trials information technology environment contributes to this situation. Clinical trials are information-intensive processes—in fact, information is their only product. Despite this, there is no comprehensive information management solution available. Instead there are many vendors, each providing tools that address different pieces of the problem. Many of these are good products that have a role to play, but they do not provide a way of integrating or managing information across the trial process.

The presently available automation tools include those that fall into the following major categories:

Clinical data capture (CDC)
Site-oriented trial management
Electronic Medical Records (EMRs) with Trial-Support Features
Trial Protocol design tools
Site-sponsor matching services
Clinical data management
Clinical Research Organizations (CROs) and Site Management Organizations (SMOs) also provide some information services to trial sites and sponsors.

1. Clinical Data Capture (CDC) Products

These products are targeted at trial sites, aiming to improve speed and accuracy of data entry. Most are rapidly moving to Web-based architectures. Some offer off-line data entry, meaning that data can be captured while the computer is disconnected from the Internet. Most companies can point to half a dozen pilot sites and almost no paying customers.

These products do not create an overall, start-to-finish, clinical trials management framework. These products also see "trial design" merely as "CRF design," ignoring a host of services and value that can be provided by a comprehensive clinical trials system. They also fail to make any significant advance over conventional methods of treating each trial as a "one-off" activity. For example, the companies offering CDC products continue to custom-design each CRF for each trial, doing not much more than substituting HTML code for printed or word-processor forms.

2. Site-Oriented Trial Management

These products are targeted at trial sites and trial sponsors, aiming to improve trial execution through scheduling, financial management, accrual, visit tracking. These products do not provide electronic clinical data entry, nor do they assist in protocol design, trial planning for sponsors, patient accrual or task management.

3. Electronic Medical Records (EMR) with Trial-Support Features

These products aim to support patient management of all patients, not just study patients, replacing most or all of a paper charting system. Some EMR vendors are focusing on particular disease areas, with KnowMed being a notable example in oncology.

These products for the most part do not focus specifically on the features needed to support clinical trials. They also require major behavior changes affecting every provider in a clinical setting, as well as requiring substantial capital investments in hardware and software. Perhaps because of these large hurdles, EMR adoption has been very slow.

4. Trial Protocol Design Tools

These products are targeted at trial sponsors, aiming to improve the protocol design and program design processes using modeling and simulation technologies. One vendor in this segment, PharSight, is known for its use of PK/PD (pharmacokinetic/pharacadynamic) modeling tools and is extending its products and services to support trial protocol design more broadly.

None of the companies offering trial protocol design tools provide the host of services and value that can be provided by a comprehensive clinical trials system.

5. Trial Matching Services

Some recent Web-based services aim to match sponsors and sites, based on a database of trials by sponsor and of sites' patient demographics. A related approach is to identify trials that a specific patient may be eligible for, based on matching patient characteristics against a database of eligibility criteria for active trials. This latter functionality is often embedded in a disease-specific healthcare portal such as cancerfacts.com.

6. Clinical Data Management

Two well-established products, Domain ClinTrial and Oracle Clinical, support the back-end database functionality needed by sponsors to store the trial data coming in from CRFs. These products provide a visit-specific way of storing and querying study data. The protocol sponsor can design a template for the storage of such data in accordance with the protocol's visit schema, but these templates are custom-designed for each protocol. These products do not provide protocol authoring or patient management assistance.

7. Statistical Analysis

The SAS Institute (SAS) has defined the standard format for statistical analysis and FDA reporting. This is merely a data format, and does not otherwise assist in the design or execution of clinical trial protocols.

8. Site Management Organizations (SMOs)

SMOs maintain a network of clinical trial sites and provide a common Institutional Review Board (IRB) and centralized contracting/invoicing. SMOs have not been making significant technology investments, and in any event, do not offer trial design services to sponsors.

9. Clinical Research Organizations (CROs)

CROs provide, among other services, trial protocol design and execution services. But they do so on substantially the same model as do sponsors: labor-intensive, paper-based, slow, and expensive. CROs have made only limited investments in information technology.

E. The Need for a Comprehensive Clinical Trials System

It can be seen that the current information model for clinical trials is highly fragmented. This has led to high costs, "noisy" data, and long trial times. Without a comprehensive, service-oriented information solution it is very hard to get away from the current paradigm of paper, faxes and labor-intensive processes. And it has become clear that simply "throwing more bodies" at trials will not produce the required results, particularly as trial throughput demands increase. A new, comprehensive model is required.

SUMMARY OF THE INVENTION

According to the invention, roughly described, clinical trials are defined, managed and evaluated according to an overall end-to-end system solution which starts with the creation of protocol meta-models by a central authority, and ends with the conduct of trials by clinical sites, who then report back electronically for near-real-time monitoring by study sponsors and for analysis by the central authority. The central authority first creates protocol meta-models, one for each of several different disease categories, and makes them available to protocol designers. Each meta-model includes a short list of preliminary patient eligibility attributes which are appropriate for a particular disease category. The protocol designer chooses the meta-model and preliminary eligibility list appropriate for the relevant disease category, and encodes the clinical trial protocol, including eligibility and patient workflow, within the selected meta-model. The resulting protocol database is stored together with databases of other protocols in the same and different disease categories, in a library of protocol databases maintained by the central authority. Sponsors and individual clinical sites have access to only the particular protocols for which they are authorized.

Study sites optionally use a two-stage screening procedure in order to identify clinical studies for which individual patients are eligible, and patients who are eligible for individual clinical studies. The study sites make reference to the protocol databases to which they have access in the protocol database library in order to make these determinations. In one embodiment the data that is gleaned from patients being screened is retained in a patient-specific database of patient attributes, or in other embodiments the data can be stored anonymously or discarded after screening. Once a patient is enrolled into a study, the protocol database indicates to the clinician exactly what tasks are to be performed at each patient visit. These tasks can include both patient management tasks, such as administering a drug or taking a measurement, and also data management tasks, such as completing and submitting a particular CRF. The workflow graph embedded in the protocol database advantageously also instructs the proper time for the clinician to obtain informed consent from a patient during the eligibility screening process, and when to perform future tasks, such as the acceptable date range for the next patient visit.

The system keeps track of the progress of the patient and the clinician through the workflow graph of a particular protocol. The system reports this information to study sponsors, who can then monitor the progress of an overall clinical trial in near-real-time, and to the central authority which can then generate performance metrics. Advantageously, a common controlled medical terminology database is used by all components of the system in order to ensure consistent usage of medical terminology by all the participants. The protocol database is advantageously used also to drive other kinds of problem-solving methods, such as an accrual simulation tool and a Find-Me-Patients tool.

BRIEF DESCRIPTION OF THE DRAWINGS

The invention will be described with respect to specific embodiments thereof, and reference will be made to the drawings, in which:

FIGS. 2-8 are screen shots of an example for an Intelligent Clinical Protocol (iCP) database.

FIGS. 11-25 are screen shots of screens produced by Protégé 2000, and will help illustrate the relationship between a protocol meta-model and an example individual clinical trial protocol.

DETAILED DESCRIPTION

Figure 1:
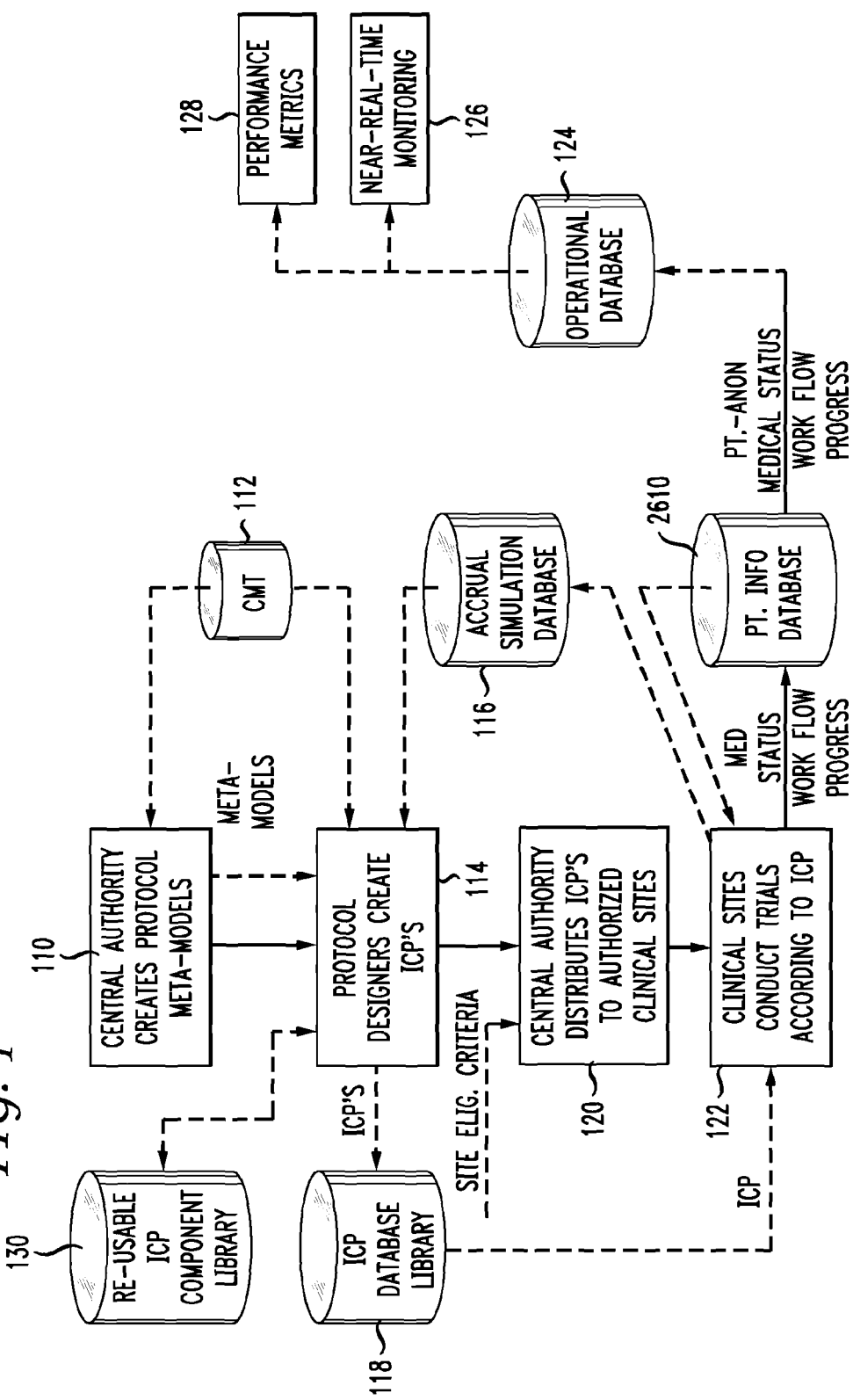
FIG. 1 is a symbolic block diagram illustrating significant aspects of a clinical trials management system and method incorporating features of the invention.

FIG. 1 is a symbolic block diagram illustrating significant aspects of a clinical trials management system and method incorporating features of the invention. In the figure, solid arrows indicate process flow, whereas broken arrows indicate information flow. In broad summary, the system is an end-to-end solution which starts with the creation of protocol meta-models by a central authority, and ends with the conduct of trials by clinical sites, who then report back electronically for near-real-time monitoring by study sponsors, for analysis by the central authority, and for use by study sponsors in identifying promising sites for future studies. As used herein, a "clinical site" can be physically at a single or multiple locations, but conducts clinical trials as a single entity. The term also includes SMOs.

Referring to FIG. 1, the central authority initially creates one or more protocol meta-models (step 110) for use in facilitating the design of clinical trial protocols. Each meta-model can be thought of as a set of building blocks from which particular protocols can be built. Preferably, the central authority creates a different meta-model for each of several disease classifications, with the building block in each meta-model being appropriate to that disease classification. In an embodiment, a meta-model is described in terms of object oriented design. The building blocks are represented as object classes, and an individual protocol database contains instances of the available classes.

The building blocks contained in a meta-model include the different kinds of steps that might be required in a trial protocol workflow, such as, for example, a branching step, an action step, a synchronization step, and so on. The available action steps for a meta-model directed to breast cancer trials might differ from the available action steps in a meta-model directed to prostate cancer trials, for example, by making available only those kinds of steps which might be appropriate for the particular disease category. For example, a step of brachytherapy might be available in the prostate cancer meta-model, but not in the breast cancer meta-model; and a step of mammography might be available in the breast cancer meta-model, but not in the prostate cancer meta-model.

The meta-models also include lists, again appropriate to the particular disease category, within which a protocol designer can define preliminary criteria for the eligibility of patients for a particular study. These preliminary eligibility criteria lists do not preclude a protocol designer from building further eligibility criteria into any particular clinical trial protocol. As set forth in more detail below, the options available in the lists of preliminary eligibility criteria are intentionally limited in number so as to facilitate the building of a large database of potential patients for studies within the particular disease area. At the same time, however, it is also desirable that the options be numerous or narrow enough in order to provide a good first cut of eligible patients. In order to best satisfy these two competing goals, it is desirable that an expert or a team of experts knowledgeable about the particular disease category of a particular meta-model be heavily involved in the development of the preliminary eligibility criteria lists for the particular meta-model. In addition, because of the difficulty and length of time required to develop a large database of potential patients, it is further desirable that once the eligibility criteria options are established for a particular meta-model, they do not change except as absolutely necessary. Such changes might be mandated as a result of improved understanding of a disease, for example, and are rigorously managed throughout the overall system of FIG. 1.

Table I sets forth example Preliminary Eligibility Criteria lists for five disease categories, specifically breast cancer, small cell lung cancer, non-small cell lung cancer, colorectal cancer and prostate cancer. As can be seen, each list includes a small number of patient attributes, each with a set of available choices from which the protocol designer can choose, in order to encode preliminary eligibility criteria for a particular protocol. The protocol meta-model for breast cancer, for example, includes the list of attributes and the list of available choices for each attribute, as shown in the row of the table for "Breast Cancer."

TABLE I

Example Preliminary Eligibility Criteria Lists

| Disease | QS attribute | Choices |
| --- | --- | --- |
| Breast cancer | Current Stage | O, I, II (IIA, IIB), III (IIIA, IIIB), IV |
| | Prior Chemo | None, Neoadj/Adj, Tx Adv Disease |
| | Prior RT | None, Primary tumor, Metastatic Dz |
| | Prior Surgery | Y, N |
| | Prior Hormonal | None, Neoadj/Adj, Tx Adv Disease |
| Lung cancer, small cell | Current Stage | Limited, Extensive |
| | Prior Chemo | None, Neoadj/Adj, Tx Adv Disease |
| | Prior RT | None, Primary tumor, Metastatic Dz |
| | Prior Surgery | Y, N |
| Lung cancer, non-small cell | Current Stage | O, I (IA, IB), II (IIA, IIB), IIIA, IIIB, IV |
| | Prior Chemo | None, Neoadj/Adj, Tx Adv Disease |
| | Prior RT | None, Primary tumor, Metastatic Dz |
| | Prior Surgery | Y, N |

TABLE I-continued

Example Preliminary Eligibility Criteria Lists

| Disease | QS attribute | Choices |
| --- | --- | --- |
| Colorectal cancer | Current Stage | O, I, II, III, IV |
| | Prior Chemo | None, Neoadj/Adj, Tx Adv Disease |
| | Prior RT | None, Primary tumor, Metastatic Dz |
| | Prior Surgery | Y, N |
| Prostate cancer | Metastases | Y, N |
| | Primary Tumor | N/A, T0, T1a, T1b, T1c, T2 (T2a, T2b), T3 (T3a, T3b), T4 |
| | Nodes | N/A, N0, N1 |
| | Prior Chemo | None, Neoadj/Adj, Tx Adv Disease |
| | Prior RT | None, Primary tumor, Metastatic Dz |
| | Prior Surgery | Y, N |
| | Prior Hormonal | None, Neoadj/Adj, Tx Adv Disease |

In the embodiment illustrated by Table I, the designer encodes preliminary eligibility criteria by assigning one of the available choices to each of at least a subset of the attributes in the selected list. Each "criterion" is defined by an attribute and its assigned value, so that a patient satisfies the criterion only if the patient has the specified value for that attribute. Each criterion is then classified either as an "inclusion" criterion or an "exclusion" criterion; a patient must satisfy all the inclusion criteria and none of the exclusion criteria in order to pass preliminary eligibility.

The logic of the preliminary eligibility criteria is capable of many variations in different embodiments. In one embodiment, for example, the designer is permitted to assign more than one of the available values to a given attribute. In this case, a patient who has any of the assigned values for the given attribute satisfies the criterion. In another embodiment, one or more of the available values for a given attribute can be specified as a numeric range, and the designer can assign any value or sub-range of values within that range to the attribute. In addition, the condition for satisfying the criterion can be specified by the designer to be something other that equality (e.g., "attribute having a value less than N", or "attribute having a value greater than N".) Speaking more generally, each criterion is defined by an attribute and a "condition", and the patient must satisfy the condition with respect to that attribute in order to satisfy the criterion.

Applicants believe that one of the reasons why in the past it has been difficult to create tools which are useful throughout the clinical trials design, execution and analysis processes, as shown in FIG. 1, is that each tool presently available maintains its data in a different format, and because there is no consistency among the different tools regarding such important questions as what is meant by a particular medical term according to which the data is maintained. The problem of consistent medical terminology is one that extends well beyond the field of clinical trials, and has spawned significant academic discourse within the field of medical informatics. As examples, see the entire November 1998 issue of "Methods of Information in Medicine", Vol. 37, No. 4-5, which is incorporated herein by reference in its entirety. See in particular the following articles: "Editorial: the Concepts of Language and the Language of Concepts", by J. J. Cimino (p. 311); "Desiderata for Controlled Medical Vocabularies in the Twenty-First Century", by J. J. Cimino (pp. 394-403); "Concept-Oriented Standardization and Statistics-Oriented Classification: Continuing the Classification Versus Nomenclature Controversy", by J. Ingenerf and W. Giere (pp. 527-539); and "Standards to Support Development of Terminological Systems for Health Care Telematics", by A. Rossi Mori, F. Consorti and E. Galeazzi (pp. 551-563). See also, Broverman, "Overview of Controlled Clinical Terminologies", slides for CME course, Aug. 18, 1999, incorporated herein by reference.

The work on terminology consistency problems has yielded a number of different databases of medical concepts, terms and attributes, none of which have been intended for use in the field of clinical trial protocols but most of which can provide some benefit in that field. These terminology databases, sometimes referred to herein as "controlled medical terminologies" (CMTs), include interface terminologies intended to support navigation for structured data entry, reference terminologies intended to support aggregation and analysis of medical data, and administrative terminology intended to support reporting and billing requirements. Interface terminologies, which include such terminologies as MEDCIN, Oceania CKB, and Purkinjie, are patient-dependent terminologies, are easily navigable to support workflow, and provide groupings of observations by context. Reference terminologies, which include SNOMED, LOINC, Meddra, and Read, are patient-independent terminologies. They are intended to completely cover a domain of discourse. They include definitions of logical concepts and are organized into hierarchies of semantic classifications. Administrative terminologies, which include ICD-9 and CPT-4, are also patient-independent. They are designed primarily for reporting and billing requirements and do not contain formal definitions. They are organized hierarchically, but only to a limited extent. In addition to the classification of CMTs as interface terminologies, reference terminologies or administrative terminologies, some of the existing CMTs (such as SNOMED) are better at covering medical diagnoses than others, and others (such as CPT-4) are better at covering the domain of medical procedures. Meddra is better at covering the field of adverse events reporting, having been developed by the Food and Drug Administration primarily for post-market surveillance of drug usage experience. All of the above-mentioned CMTs are incorporated by reference herein.

The overall clinical trials process illustrated in FIG. 1 is performed by a wide variety of different people, all of whom might have different understandings about the meaning of various concepts, terms and attributes. Therefore, in order for all the different steps and tools to work well together, the system of FIG. 1 takes advantage of a CMT 112 wherever possible. For example, most if not all of the concepts, terms and attributes which are used in the workflow task building blocks and patient eligibility criteria options made available in the meta-models produced in step 110, are entries in the CMT 112. In one embodiment, a meta-model contains copies of the relevant entries from the CMT 112, whereas in another embodiment, the meta-models contain merely pointers to the relevant entries in CMT 112. A meta-model designer or protocol author preferably uses a CMT browser to select desired CMT entries for inclusion in a meta-model or protocol.

The CMT 112 can be any of the CMTs presently existing, or can be a new CMT altogether. Preferably, CMT 112 includes entries developed from several of the different presently existing CMTs, as well as additional entries which are appropriate for clinical trial protocols, and for the particular disease categories covered by the various meta-models produced in step 110. Preferably CMT 112 is organized hierarchically by concept. Each concept includes pointers to one or more terms which describe the concept synonymously. For example, the concept "hypertension" might have pointers to the terms "hypertension", "elevated blood pressure", and "high blood pressure". Each concept also includes pointers to one or more attributes. The "hypertension" concept, for example, might include a pointer to an attribute, "diastolic blood pressure greater than 95 mm Hg," where "blood pressure" is itself a concept and is represented by a pointer back to the list of concepts.

The step 110 of creating protocol meta-models is performed using a meta-model authoring tool, Protégé 2000 is an example of a tool that can be used as a meta-model authoring tool. Protégé 2000 is described in a number of publications including William E. Grosso, et. al., "Knowledge Modeling at the Millennium (The Design and Evolution of Protégé-2000)," SMI Report Number: SMI-1999-0801 (1999), available at http://smi-web.stanford.edu/pubs/SMI_Abstracts/SMI-1999-0801.html, visited Jan. 1, 2000, incorporated by reference herein. In brief summary, Protégé 2000 is a tool that helps users build other tools that are custom-tailored to assist with knowledge-acquisition for expert systems in specific application areas. It allows a user to define "generic ontologies" for different categories of endeavor, and then to define "domain-specific ontologies" for the application of the generic ontology to more specific situations. In many ways, Protégé 2000 assumes that the different generic ontologies differ from each other by major categories of medical endeavors (such as medical diagnosis versus clinical trials), and the domain-specific ontologies differ from each other by disease category. In the present embodiment, however, all ontologies are within the category of medical endeavor known as clinical trials and protocols. The different generic ontologies correspond to the different meta-models produced in step 110 (FIG. 1), which differ from each other by disease category. In this sense, the generic ontologies produced by Protégé in step 110 are directed to a much more specific domain than those produced in other applications of Protégé 2000.

Since the meta-models produced in step 110 include numerous building blocks as well as many options for patient eligibility criteria, a wide variety of different kinds of clinical trial protocols, both simple and complex, can be designed. These meta-models are provided to clinical trial protocol designers who use them, preferably again with the assistance of Protégé 2000, to design individual clinical trial protocols in step 114.

In step 114 of FIG. 1, a protocol designer desiring to design a protocol for a clinical trial in a particular disease category, first selects the appropriate meta-model and then uses the authoring tool to design and memorialize the protocol. As in step 110, one embodiment of the authoring tool for step 114 is based on Protégé 2000. The output of step 114 is a database which contains all the significant required elements of a protocol. This database is sometimes referred to herein as an Intelligent Clinical Protocol (iCP) database, and provides the underlying logical structure for driving much of the processes that take place in the remainder of FIG. 1.

Conceptually, an iCP database is a computerized data structure that encodes most significant aspects of a clinical protocol, including eligibility criteria, randomization options, treatment sequences, data requirements, and protocol modifications based on patient outcomes or complications. The iCP structure can be readily extended to encompass new concepts, new drugs, and new testing procedures as required by new drugs and protocols. The iCP database is used by most software modules in the overall system to ensure that all protocol parameters, treatment decisions, and testing procedures are followed.

The iCP database can be thought of as being similar to the CAD/CAM tools used in manufacturing. For example, a CAD/CAM model of an airplane contains objects which represent various components of an airplane, such as engines, wings, and fuselage. Each component has a number of additional attributes specific to that component—engines have thrust and fuel consumption; wings have lift and weight. By constructing a comprehensive model of an airplane, numerous different types of simulations can be executed using the same model to ensure consistent results, such as flight characteristics, passenger/revenue projections, maintenance schedules. And finally, the completed CAD/CAM simulations automatically produced drawings and manufacturing specifications to accelerate actual production. While an iCP database differs from the CAD/CAM model in important ways, it too provides a comprehensive model of a clinical protocol so as to support consistent tools created for problems such as accrual, patient screening and workflow management. By using a comprehensive model and a unifying standard vocabulary, all tools behave according to the protocol specifications.

As used herein, the term "database" does not necessarily imply any unity of structure. For example, two or more separate databases, when considered together, still constitute a "database" as that term is used herein.

As described in more detail below, the iCP data structures can be used by multiple tools to ensure that the tool performs in strict compliance with the clinical protocol requirements. For example, a patient recruitment simulation tool can use the eligibility criteria encoded into an iCP data structure, and a workflow management tool uses the visit-specific task guidelines and data capture requirements encoded into the iCP data structure. The behavior of all such tools will be consistent with the protocol because they all use the same iCP database.

Many clinical systems provide a "dumb database" for patient data, but offer no intelligence, no automation. While these systems may offer some efficiency benefits compared to paper systems, they are incapable of driving workflow management, sophisticated data validation or recognizing protocol-critical patterns in patient data (e.g. a toxic response to a drug that should trigger a modification to the treatment). A few systems have used rule-based expert systems or other technologies to deliver more intelligence to clinicians, but these have encountered significant problems: huge up-front modeling costs and ongoing maintenance costs; unpredictable system behavior over time; and an inability to reuse knowledge content or software components. So the choices available for clinical investigators have been poor: use paper, use an electronic file cabinet with no intelligence, or build a custom intelligent system for each trial. The use of an iCP database and a variety of tools designed to be driven by an iCP database overcomes many of the deficiencies with the prior art options.

The iCP database is used to drive all downstream "problem solvers" such as electronic case report forms, and assures that those applications are revised automatically as the protocol changes. This assures protocol compliance. The iCP authoring tool draws on external knowledge bases to help trial designers, and creates a library of re-usable protocol "modules" that can be incorporated in new trials, saving time and cost and enabling a clinical trial protocol design process that is more akin to customization than to the current "every trial unique" model.

Figure 11:
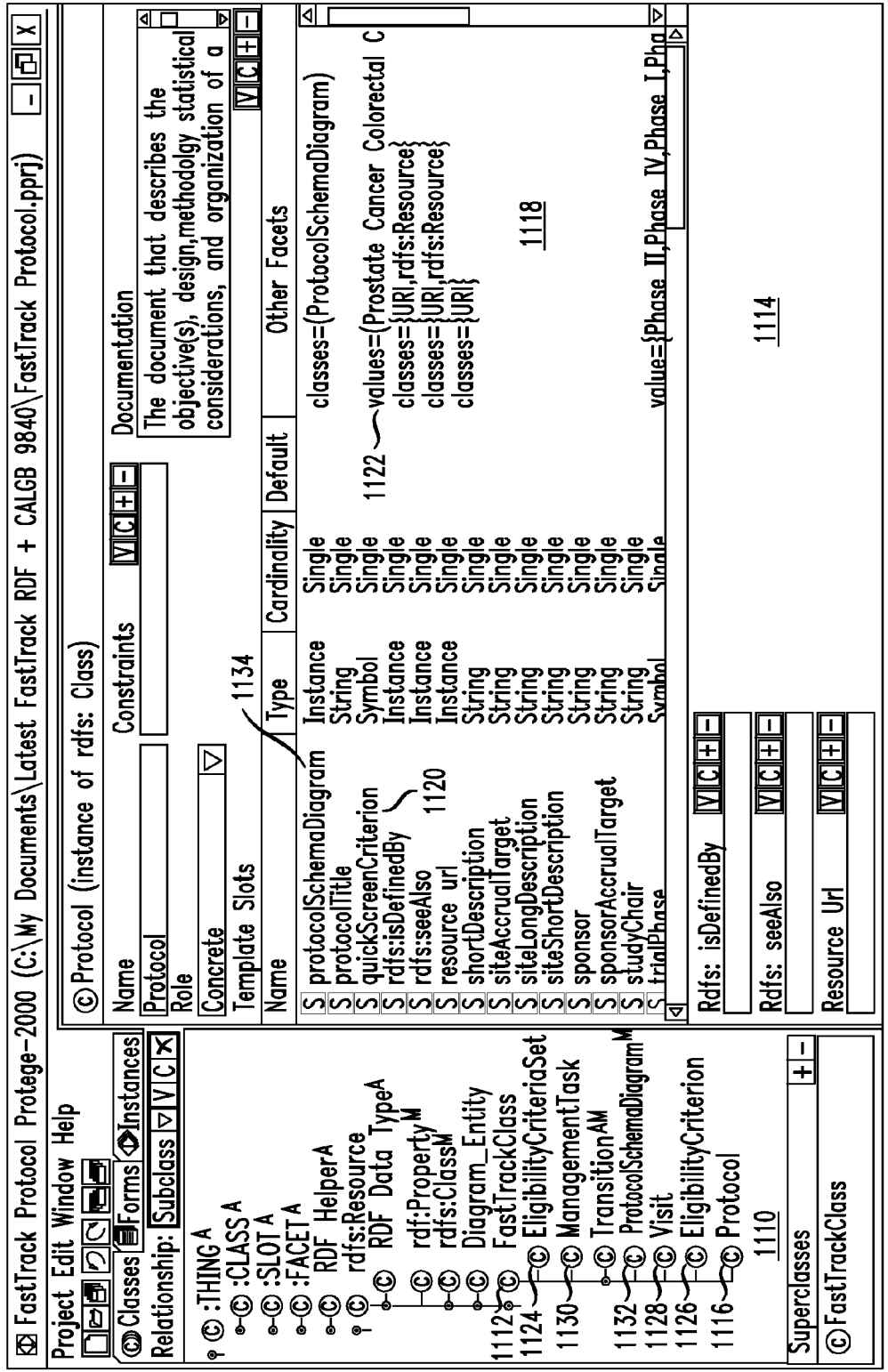

FIGS. 11-25 are screen shots of screens produced by Protégé 2000, and will help illustrate the relationship between a protocol meta-model and an example individual clinical trial protocol. FIG. 11 is a screen shot illustrating the overall class structure in the left-hand pane 1110. Of particular interest to the present discussion is the class 1112, called "FastTrack-Class" and the classes under class 1112. FastTrackClass 1112 and those below it represent an example of a protocol meta-model. This particular meta-model is not specific to a single disease category, but one that is specific to a single disease category is described below with respect to FIGS. 2-8.

The right-hand pane 1114 of the screen shot of FIG. 11 sets forth the various slots that have been established for a selected one of the classes in the left-hand pane 1110. In the image of FIG. 11, the "protocol" class 1116, a subclass of FastTrack-Class 1112, has been selected (as indicated by the shading). In the right-hand pane 1114, specifically in the window 1118, the individual slots for protocol class 1116 are shown. Only those indicated by a shaded "S" are pertinent to the present discussion; those indicated by an unshaded "S" are more general and not important for an understanding of the invention. It can be seen that several of the slots in the window 1118 contain "facets" which, for some slots, define a limited set of "values" that can be stored in the particular slot. For example, the slot "quickScreenCriterion" can take on only the specific values "prostate cancer," "colorectal cancer," "breast cancer," etc. These are the only disease categories for which quickScreenCriteria had been established at the time the screen shot of FIG. 11 was taken.

FIG. 12 is a screen shot of a particular instance of class "protocol" in FIG. 11, specifically a protocol object having identifier CALGB 9840. It can be seen that each of the slots defined for protocol class 1116 has been filled in with specific values in the protocol class object instance of FIG. 12. Whereas FIG. 11 illustrates an aspect of a clinical trial protocol meta-model, FIG. 12 illustrates the top-level object of an actual iCP designated CALGB 9840. Of particular note, it can be seen that for the iCP CALGB 9840, the slot "quickScreenCriterion" 1120 (FIG. 11) has been filled in by the protocol author as "Breast Cancer" (item 1210 in FIG. 12), which is one of the available values 1122 for the quickScreenCriterion slot 1120 in FIG. 11. In addition, the protocol author has also filled in "CALGB 9840 Eligibility Criteria", an instance of EligibilityCriteriaSet class 1124, for an EligibilityCriteriaSet slot (not shown in FIG. 11) of the protocol class object. Essentially, therefore, the protocol class object of FIG. 12 includes a pointer to another object identifying the "further eligibility criteria" for iCP CALGB 9840.

Figure 13:
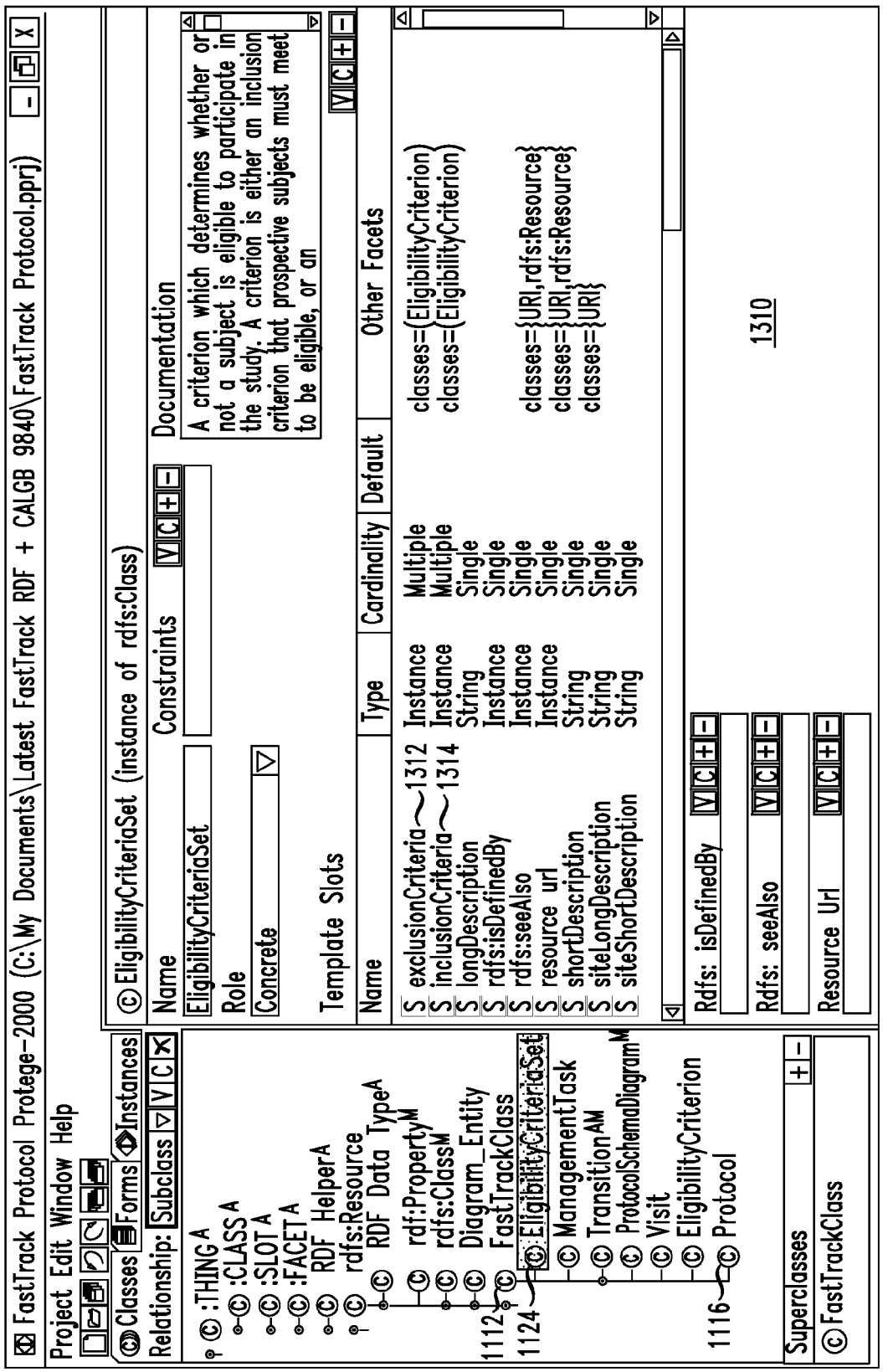

FIG. 13 illustrates in the right-hand pane 1310 the slots defined in the protocol meta-model for the class "EligibilityCriteriaSet" 1124. Of particular note is that an EligibilityCriteriaSet object will include both exclusion criteria (slot 1312) and inclusion criteria (slot 1314). It can be seen from FIG. 13 that the values that can be placed in slots 1312 and 1314 are objects of the class "EligibilityCriterion" 1126. It will be appreciated that in a different embodiment, other structural organizations for maintaining the same information are possible, such as a single list including all patient eligibility criteria, and flags indicating whether each criterion is an inclusion criterion or an exclusion criterion.

Figure 14:
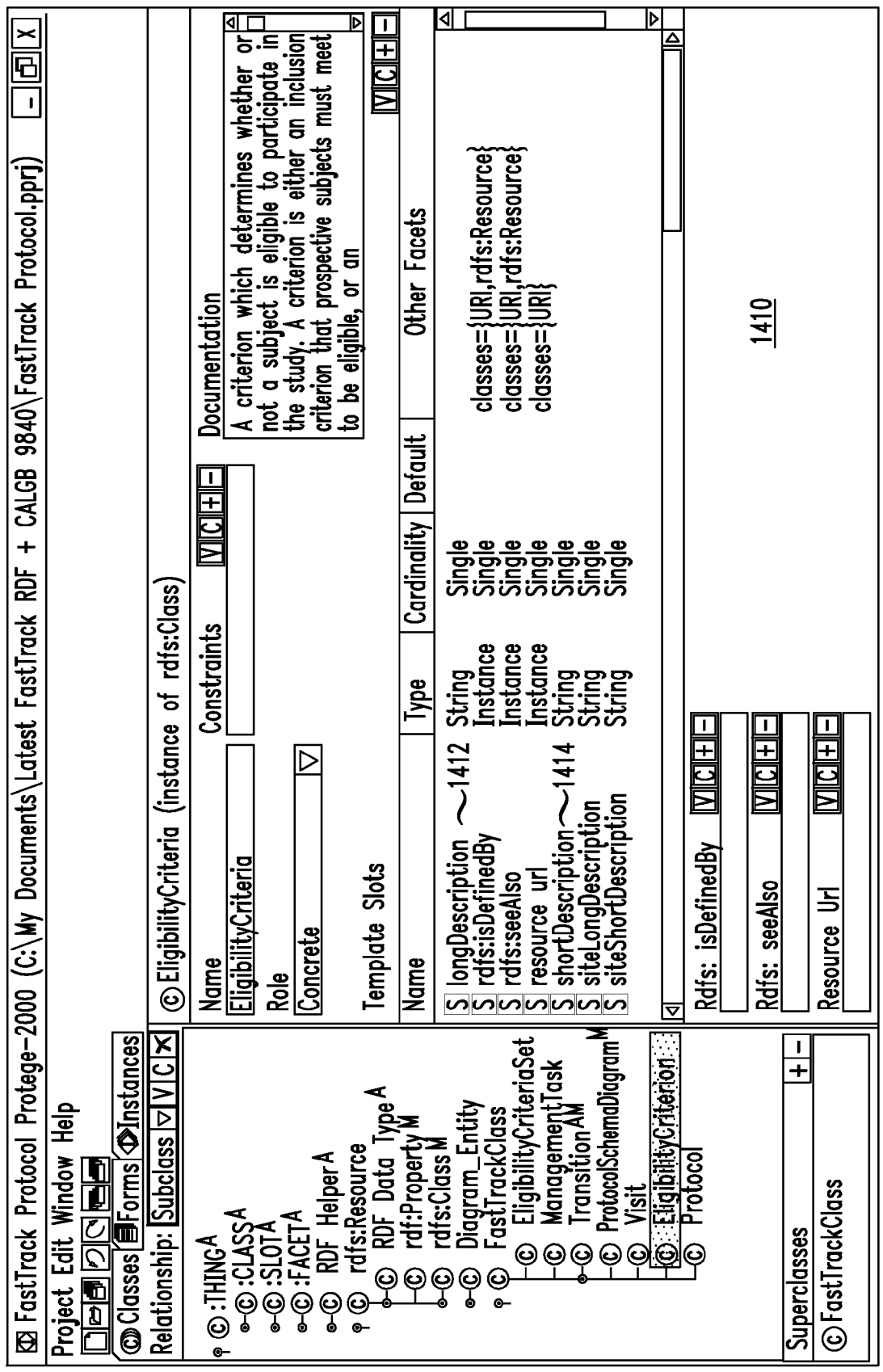

FIG. 14 illustrates in the right-hand pane 1410 the slots which can be filled in for objects of the class "EligibilityCriterion". As can be seen, these slots are merely for descriptive text strings, primarily a slot 1412 for a long description and a slot 1414 for a short description.

Figure 15:
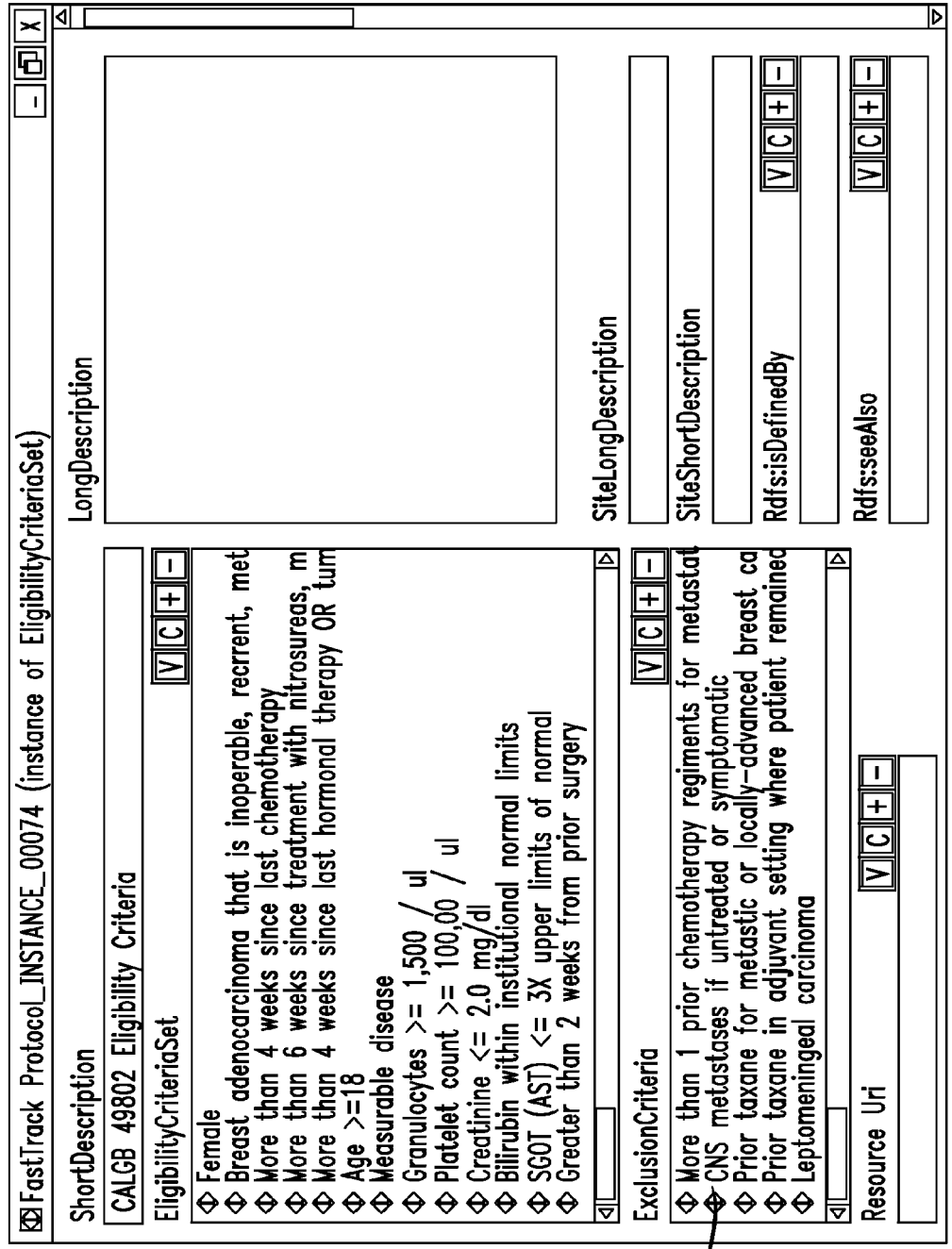
Figure 16:
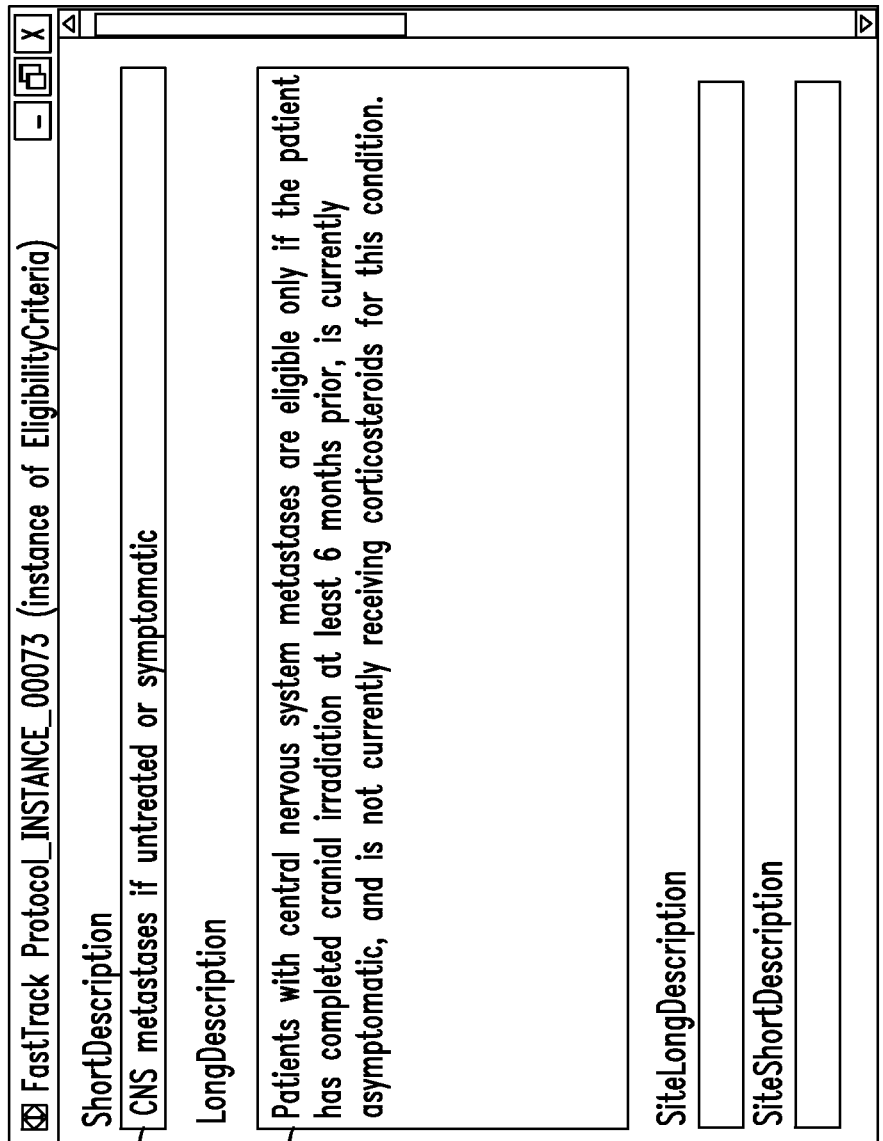

FIG. 15 illustrates the instance of the EligibilityCriteriaSet class which appears in the CALGB 9840 iCP. It can be seen that the object contains a list of inclusion criteria and a list of exclusion criteria, each criterion of which is an instance of the ElgibilityCriterion class 1126. One of such instances 1510 is illustrated in FIG. 16. Only the short description 1610 and the long description 1612 have been entered by the protocol author.

Figure 17:
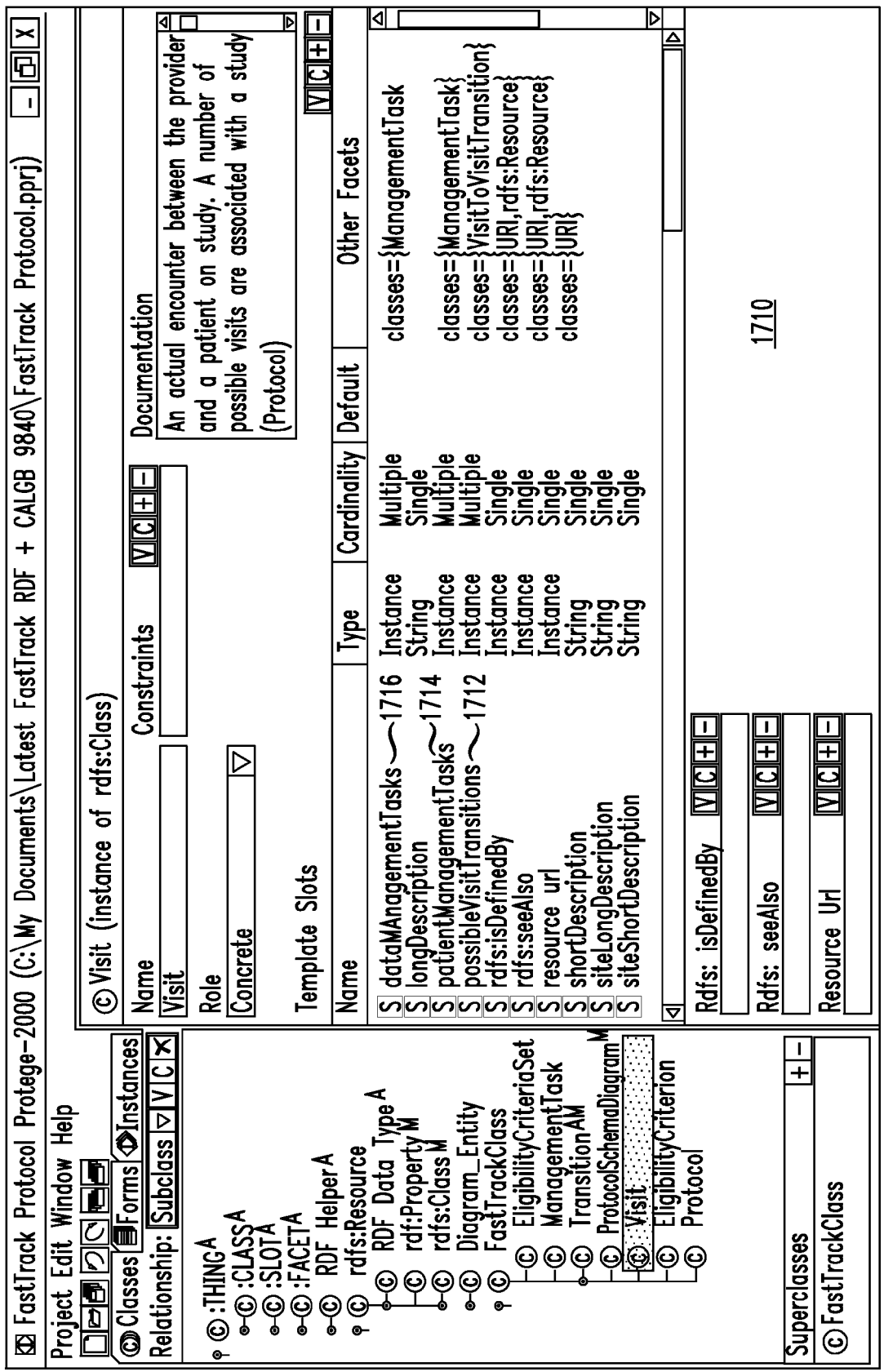

An iCP, in addition to containing a pointer (1210 in FIG. 12) to the relevant set of quickScreenCriteria, and also identifying (1212) further eligibility criteria, also contains the protocol workflow in the form of patient visits, management tasks to take place during a visit, and transitions from one visit to another. The right-hand pane 1710 of FIG. 17 illustrates the slots available for an object instance of the class "visit" 1128. It can be seen that in addition to a slot 1712 for possible visit transitions, the Visit class also includes a slot 1714 for patient management tasks as well as another slot 1716 for data management tasks. In other words, a clinical trial protocol prepared using this clinical trial protocol meta-model can include instructions to clinical personnel not only for patient management tasks (such as administer certain medication or take certain tests), but also data management tasks (such as to complete certain CRFs).

Figure 18:
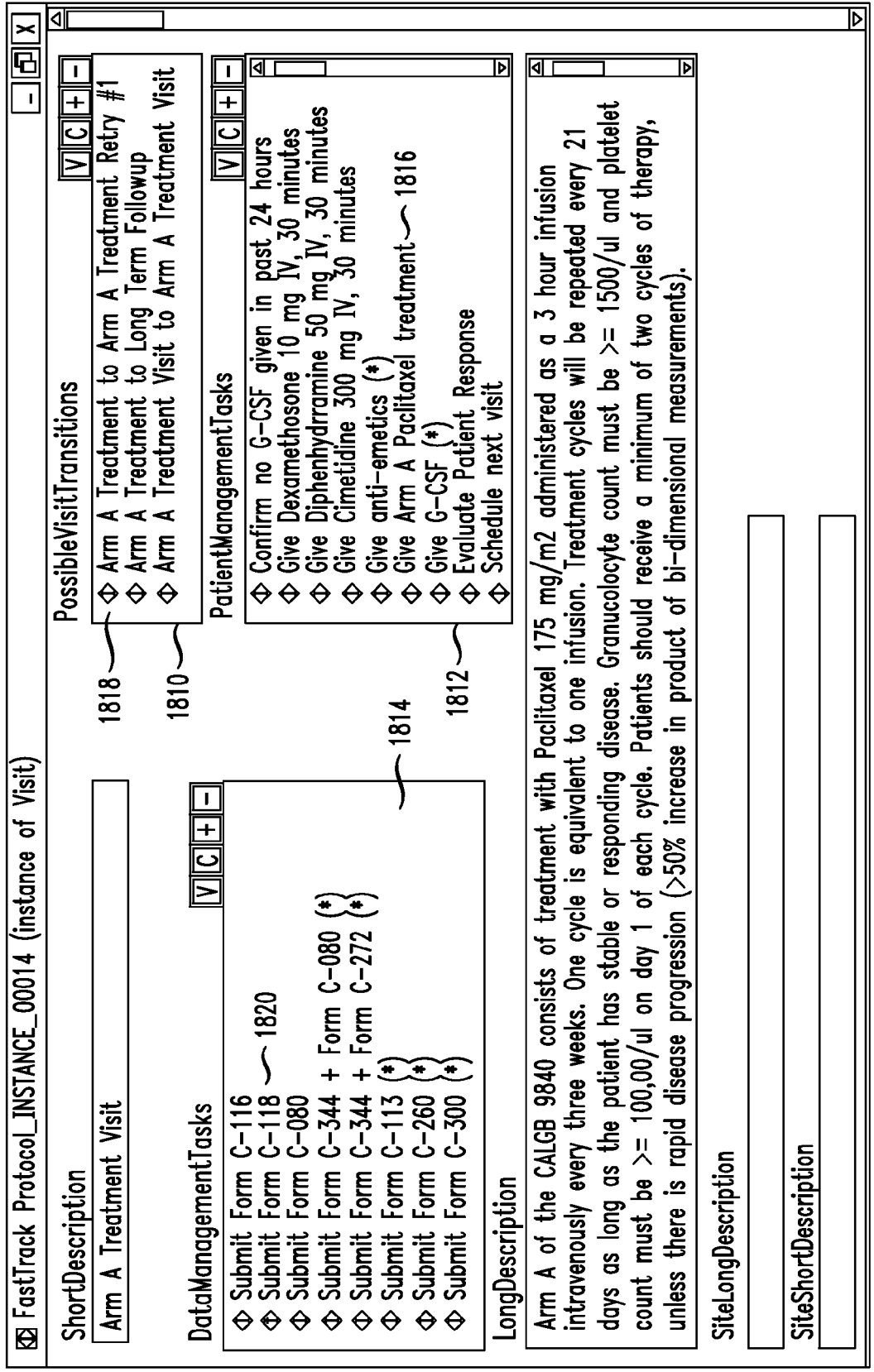
Figure 19:
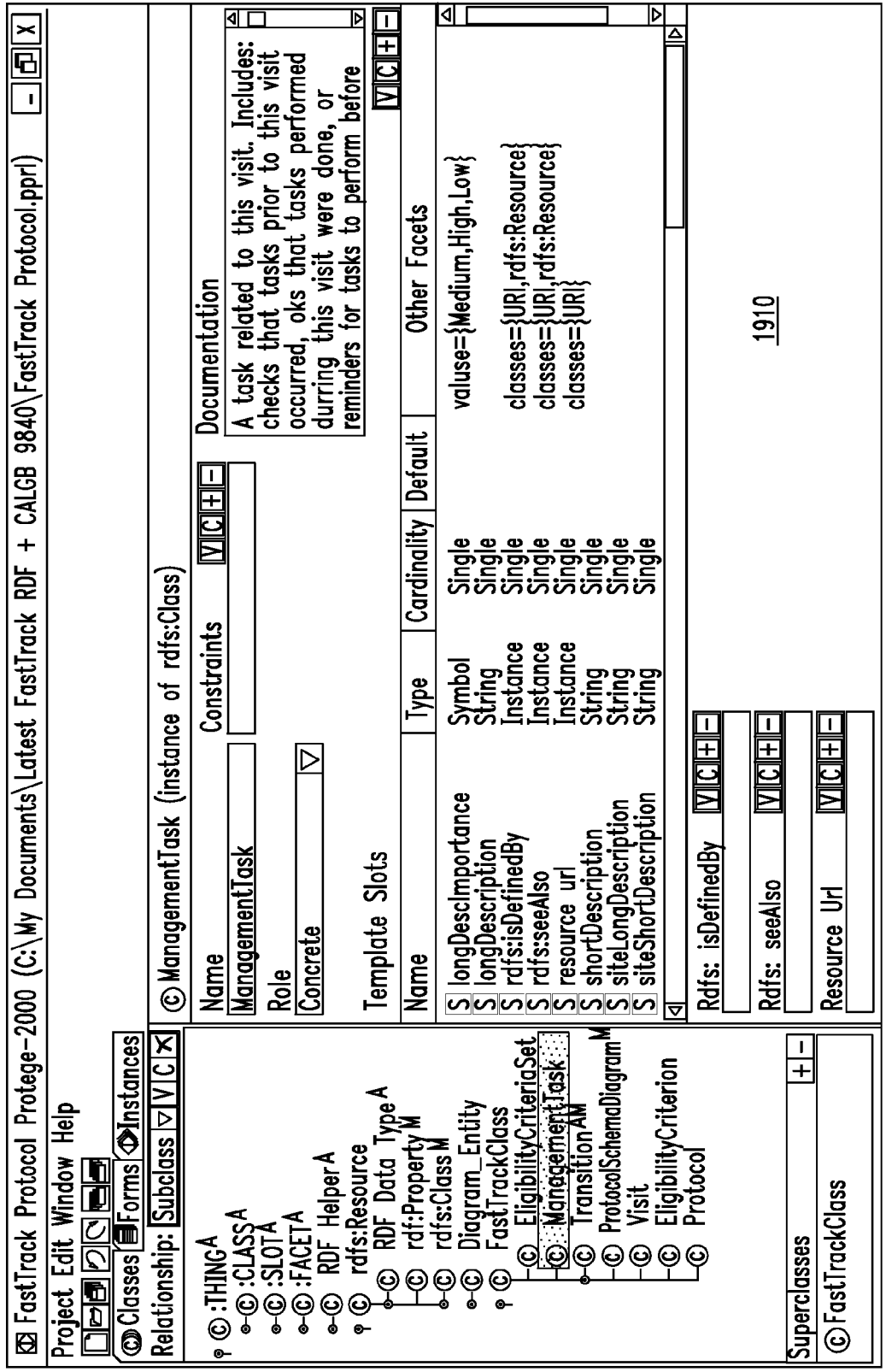
Figure 22:
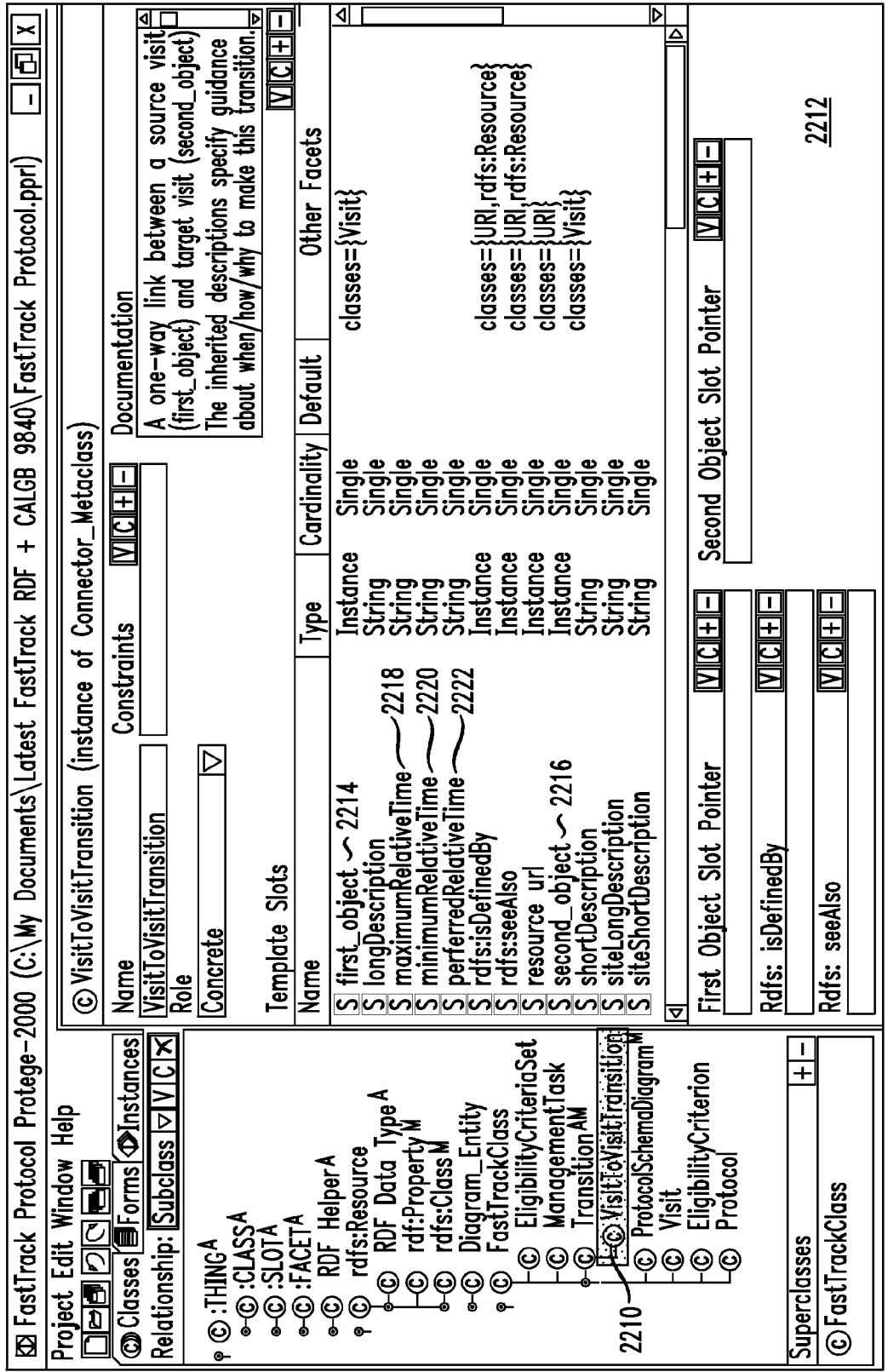

FIG. 18 illustrates a particular instance of visit class 1128, which is included in the CALGB 9840 iCP. As can be seen, it includes a window 1810 containing the possible visit transitions, a window 1812 containing the patient management tasks, and a window 1816 showing the data management tasks for a particular visit referred to as "Arm A treatment visit". The data management tasks and patient management tasks are all instance of the "ManagementTask" class 1130 (FIG. 11), the slots of which are set forth in the right-hand pane 1910 of FIG. 19. As with the EligibilityCriterion class 1126 (FIG. 14), the slots available to a protocol author in a ManagementTask object are mostly text fields.

FIG. 20 illustrates the ManagementTask object 1816 (FIG. 18), "give Arm A Paclataxel Treatment." Similarly, FIG. 21 illustrates the ManagementTask object 1818, "Submit Form C-116". The kinds of data management tasks which can be included in an iCP according to the clinical trial protocol meta-model include, for example, tasks calling for clinical personnel to submit a particular form, and a task calling for clinical personnel to obtain informed consent.

Returning to FIG. 17, the values that a protocol author places in the slot 1712 of a visit class 1128 object are themselves instances of VisitToVisitTransition class 2210 (FIG. 22) in the meta-model. The right-hand pane 2212 shows the slots which are available in an object of the VisitToVisitTransition class 2210. As can be seen, it includes a slot 2214 which points to the first visit object of the transition, another slot 2216 which points to a second visit object of the transition, and three slots 2218, 2220 and 2222 in which the protocol author provides the minimum, maximum and preferred relative time of the transition. FIG. 23 shows the contents of a VisitToVisitTransition object 1818 (FIG. 18) in the CALGB 9840 iCP.

Figure 24:
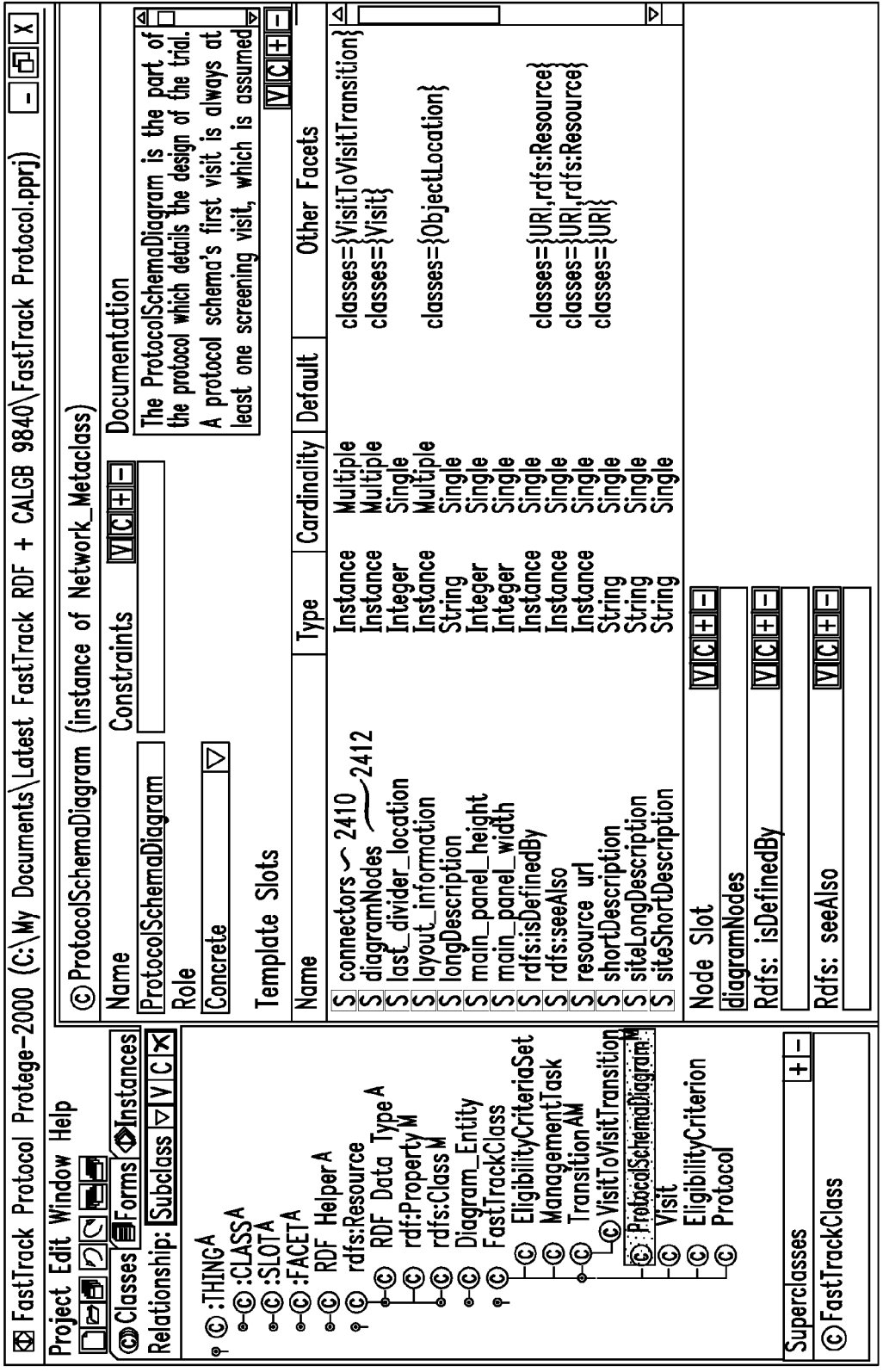
Figure 25:
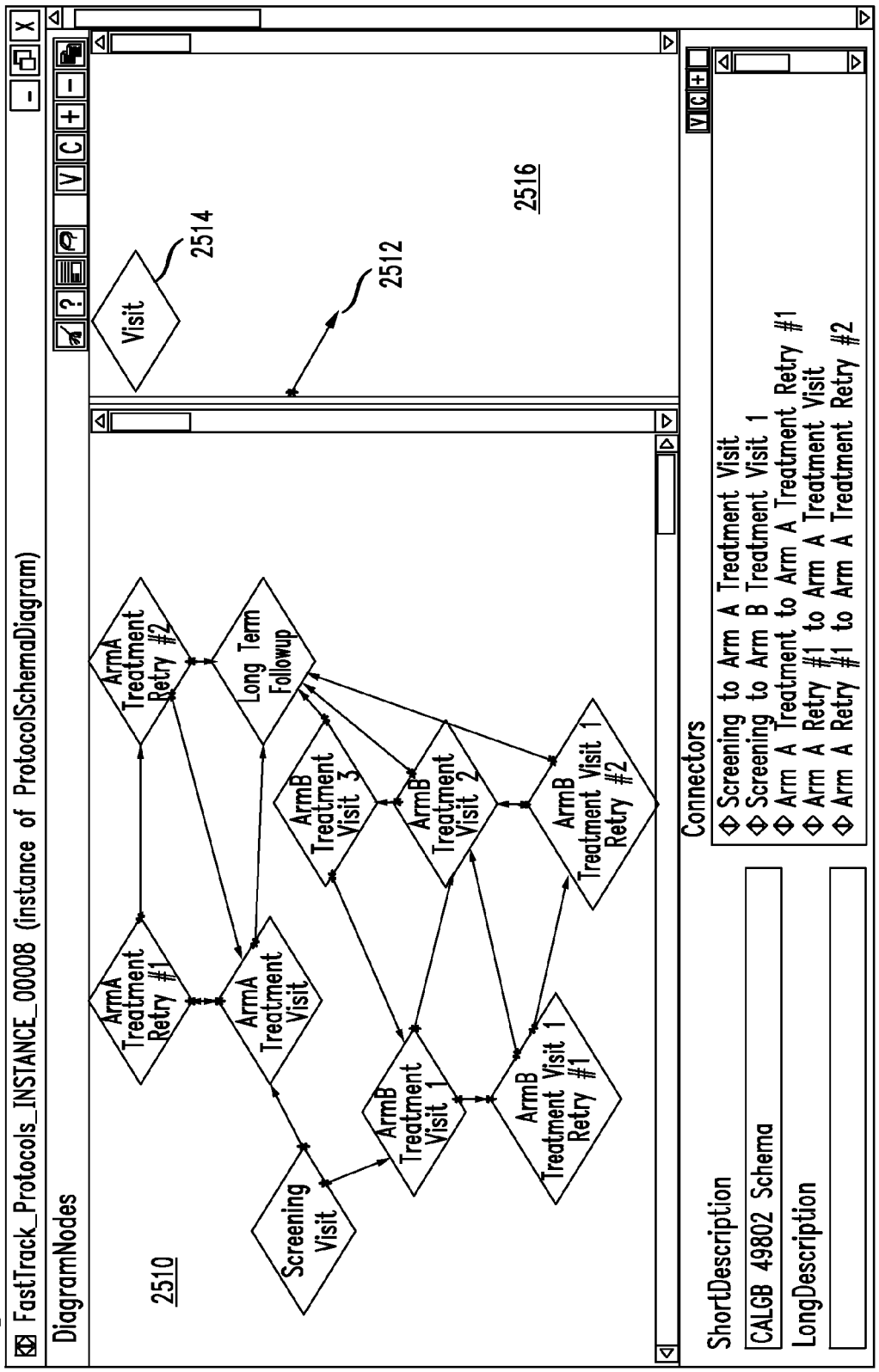

In addition to being kept in the form of Visit objects, management task objects and VisitToVisitTransition objects, the protocol meta-model also allows an iCP to keep the protocol schema in a graphical or diagrammatic form as well. In fact, it is the graphical form that protocol authors typically use, with intuitive drag-and-drop and drill-down behaviors, to encode clinical trial protocols using Protégé 2000. In the protocol meta-model, a slot 1134 is provided in the Protocol object class 1116 for pointing to an object of the ProtocolSchemaDiagram class 1132 (FIG. 1). FIG. 24 shows the slots available for ProtocolSchemaDiagram class 1132. As can be seen, they include a slot 2410 for diagrammatic connectors, and another slot 2412 for diagram nodes. The diagram connectors are merely the VisitToVisitTransition objects described previously, and the diagram nodes are merely the Visit objects described previously. FIG. 25 illustrates the ProtocolSchemaDiagram object 1214 (FIG. 12) in the CALGB 9840 iCP. It can be seen that the entire clinical trial protocol schema is illustrated graphically in pane 2510, and the available components of the graph (connector objects 2512 and visit objects 2514) are available in pane 1516 for dragging to desired locations on the graph.

FIGS. 2-8 are screen shots of another example iCP database, created and displayed by Protégé 2000 as an authoring tool. This iCP encodes clinical trial protocol labeled CALGB 49802, and differs from the CALGB 9840 iCP in that CALGB 49802 was encoded using a starting meta-model that was already specific to a specific disease area, namely cancer. It will be appreciated that in other embodiments, the meta-models can be even more disease specific, for example meta-models directed specifically to breast cancer, prostate cancer and so on.

FIG. 2 is a screen shot of the top level of the CALGB 49802 iCP database. The screen shot sets forth all of the text fields of the protocol, as well as a list 210 of patient inclusion criteria and a list 212 of patient exclusion criteria.

Figure 3:
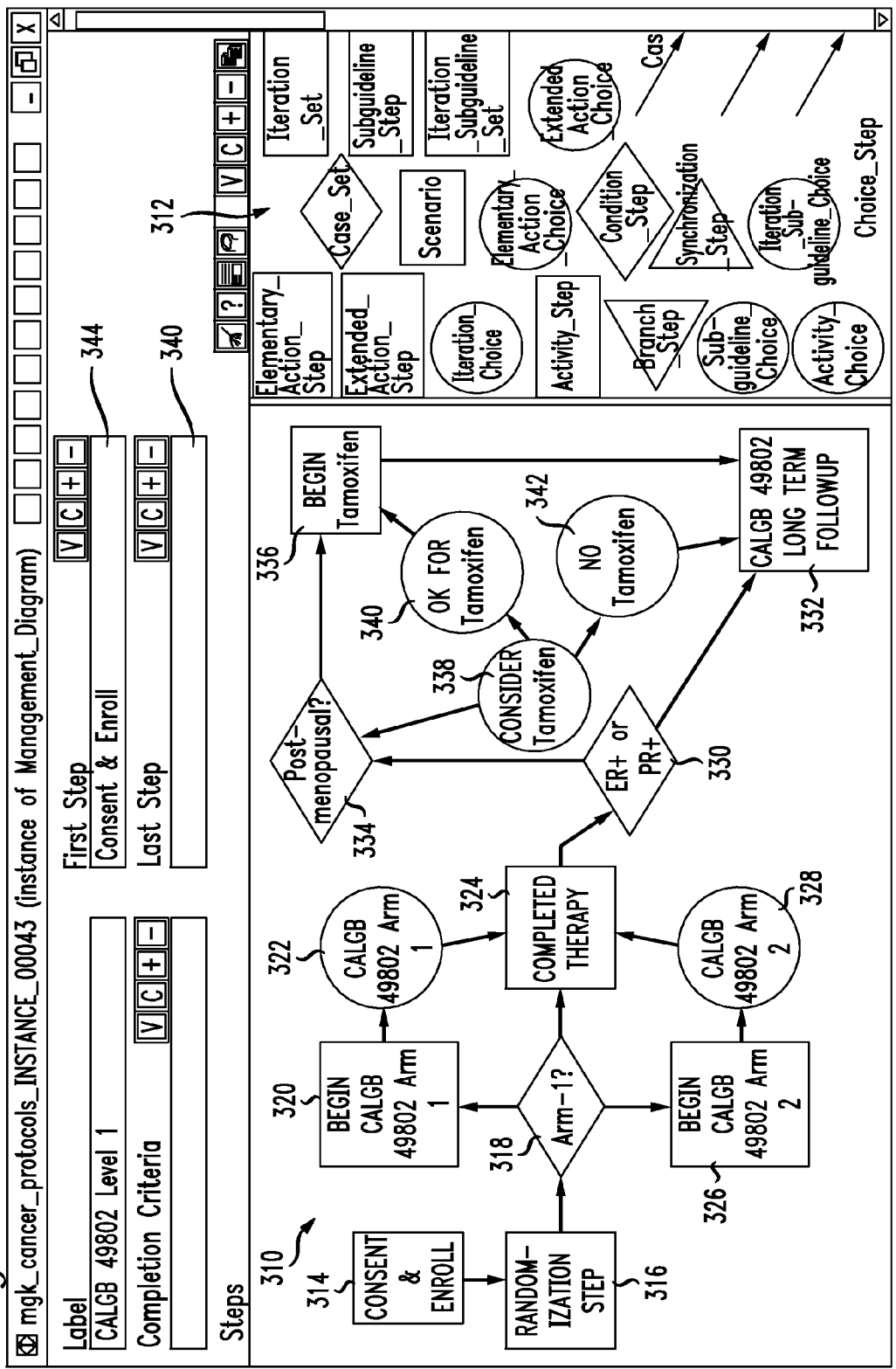

FIG. 3 is a screen shot of the Management_Diagram class object for the iCP, illustrating the workflow diagram for the clinical trial protocol of FIG. 2. The workflow diagram sets forth the clinical algorithm, that is, the sequence of steps, decisions and actions that the protocol specification requires to take place during the course of treating a patient under the particular protocol. The algorithm is maintained as sets of tasks organized as a graph 310, illustrated in the left-hand pane of the screen shot of FIG. 3. The protocol author adds steps and/or decision objects to the graph by selecting the desired type of object from the palate 312 in the right-hand pane of the screen shot of FIG. 3, and instantiating them at the desired position in the graph 310. Buried beneath each object in the graph 310 are fields which the protocol designer completes in order to provide the required details about each step, decision or action. The user interface of the authoring tool allows the designer to drill down below each object in the graph 310 by double-clicking on the desired object. The Management_Diagram object for the iCP also specifies a First Step (field 344), pointing to Consent & Enroll step 314, and a Last Step (field 346), which is blank.

Referring to the graph 310, it can be seen that the workflow diagram begins with a "Consent & Enroll" object 314. This step, which is described in more detail below, includes sub-steps of obtaining patient informed consent, evaluating the patient's medical information against the eligibility criteria for the subject clinical trial protocol, and if all such criteria are satisfied, enrolling the patient in the trial.

After consent and enrollment, step 316 is a randomization step. If the patient is assigned to Arm 1 of the protocol (step 318), then workflow continues with the "Begin CALGB 49802 Arm 1" step object 320, In this Arm, in step 322, procedures are performed according Arm 1 of the study, and workflow continues with the "Completed Therapy" step 324. If in step 318 the patient was assigned Arm 2, then workflow continues at the "Begin CALGB 49802 Arm 2" step 326. Workflow then continues with step 328, in which the procedures of protocol Arm 2 are performed and, when done, workflow continues at the "Completed Therapy" scenario step 324.

After step 324, workflow for all patients proceeds to condition_step "ER+ or PR+" step 330. If a patient is neither estrogen-receptor positive nor progesterone receptor positive, then the patient proceeds to a "CALGB 49802 long-term follow-up" sub-guideline object step 332. If a patient is either estrogen-receptor positive or progesterone receptor positive, then the patient instead proceeds to a "Post-menopausal?" condition_step object 334. If the patient is post-menopausal, then the patient proceeds to a "Begin Tamoxifen" step 336, and thereafter to the long-term follow-up sub-guideline 332.

If in step 334, the patient is not post-menopausal, then workflow proceeds to a "Consider Tamoxifen" choice_step object 338. In this step, the physician using clinical judgment determines whether the patient should be given Tamoxifen. If so (choice object 340), then the patient continues to the "Begin Tamoxifen" step object 336. If not (choice object 342), then workflow proceeds directly to the long-term follow-up sub-guideline object 332. It will be appreciated that the graph 310 is only one example of a graph that can be created in different embodiments to describe the same overall protocol schema. It will also be appreciated that the library of object classes 312 could be changed to a different library of object classes, while still being oriented to protocol-directed clinical studies.

Figure 4:
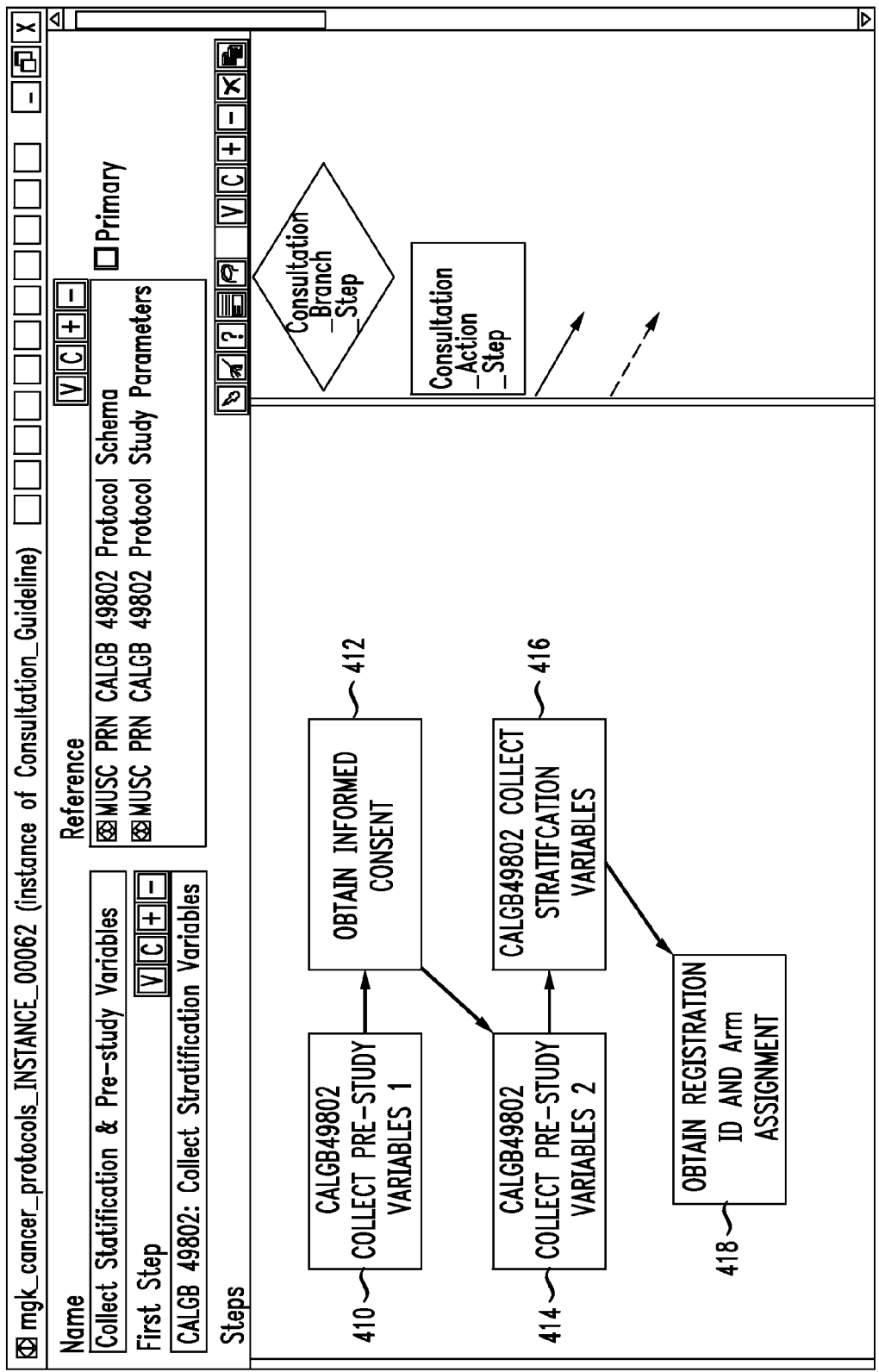

FIG. 4 is a screen shot showing the result of "drilling down" on the "Consent & Enroll" step 314 (FIG. 3). As can be seen, FIG. 4 contains a sub-graph (which is also considered herein to be a "graph" in its own right) 410. The Consent & Enroll step 314 also contains certain text fields illustrated in FIG. 4 and not important for an understanding of the invention.

As can be seen, graph 410 begins with a "collect pre-study variables 1" step object 410, in which the clinician is instructed to obtain certain patient medical information that does not require informed consent. Step 412 is an "obtain informed consent" step, which includes a data management task instructing the clinician to present the study informed consent form to the patient and to request the patient's signature. In another embodiment, the step 412 might include a sub-graph which instructs the clinician to present the informed consent form, and if it is not signed and returned immediately, then to schedule follow-up reminder telephone calls at future dates until the patient returns a signed form or declines to participate.

After informed consent is obtained, the sub-graph 410 continues at step object 414, "collect pre-study variable 2", This step instructs the clinician to obtain certain additional patient medical information required for eligibility determination. If the patient is eligible for the study and wishes to participate, then the flow continues at step object 416, "collect stratification variables", The flow then continues at step 418, "obtain registration I.D. and Arm assignment" which effectively enrolls the patient in the trial.

Figure 5:
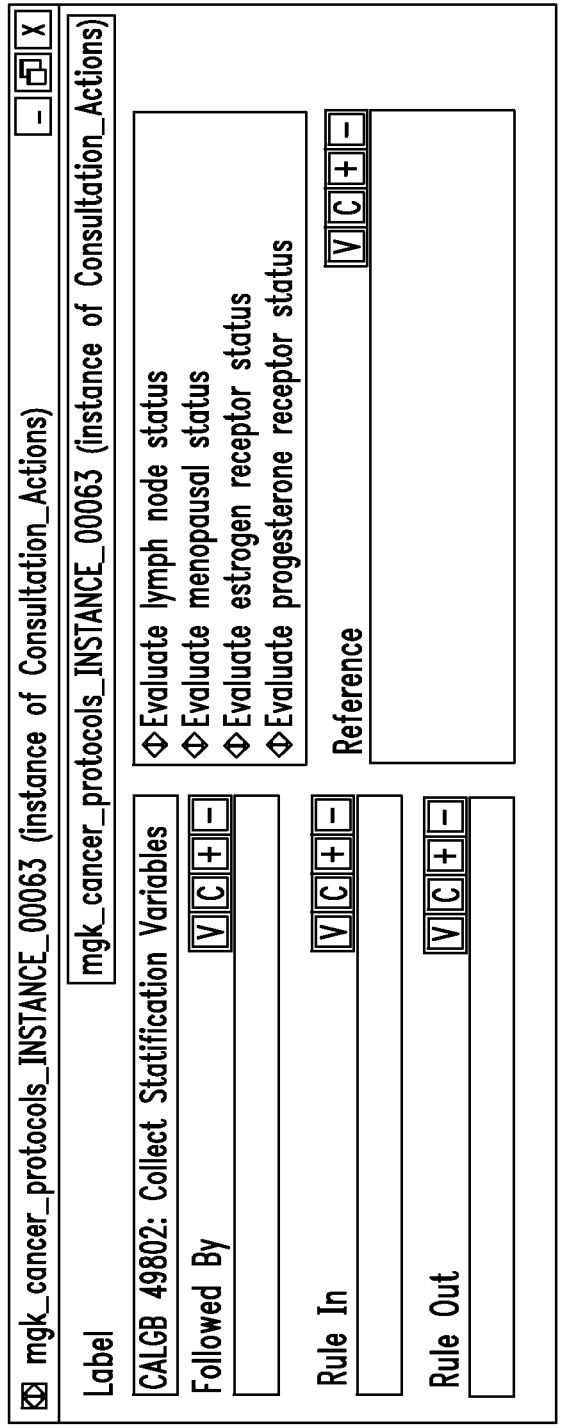

FIG. 5 is a detail of the "Collect Stratification Variables" step 416 (FIG. 4). As can be seen, it contains a number of text fields, as well as four items of information that the clinician is to collect about the subject patient. When the clinical site protocol management software reaches this stage in the workflow, it will ask the clinician to obtain these items of information about the current patient and to record them for subsequent use in the protocol. The details of the "Collect pre-study variables" 1 and 2 steps 410 and 414 (FIG. 4) are analogous, except of course the specific tasks listed are different.

Figure 6:
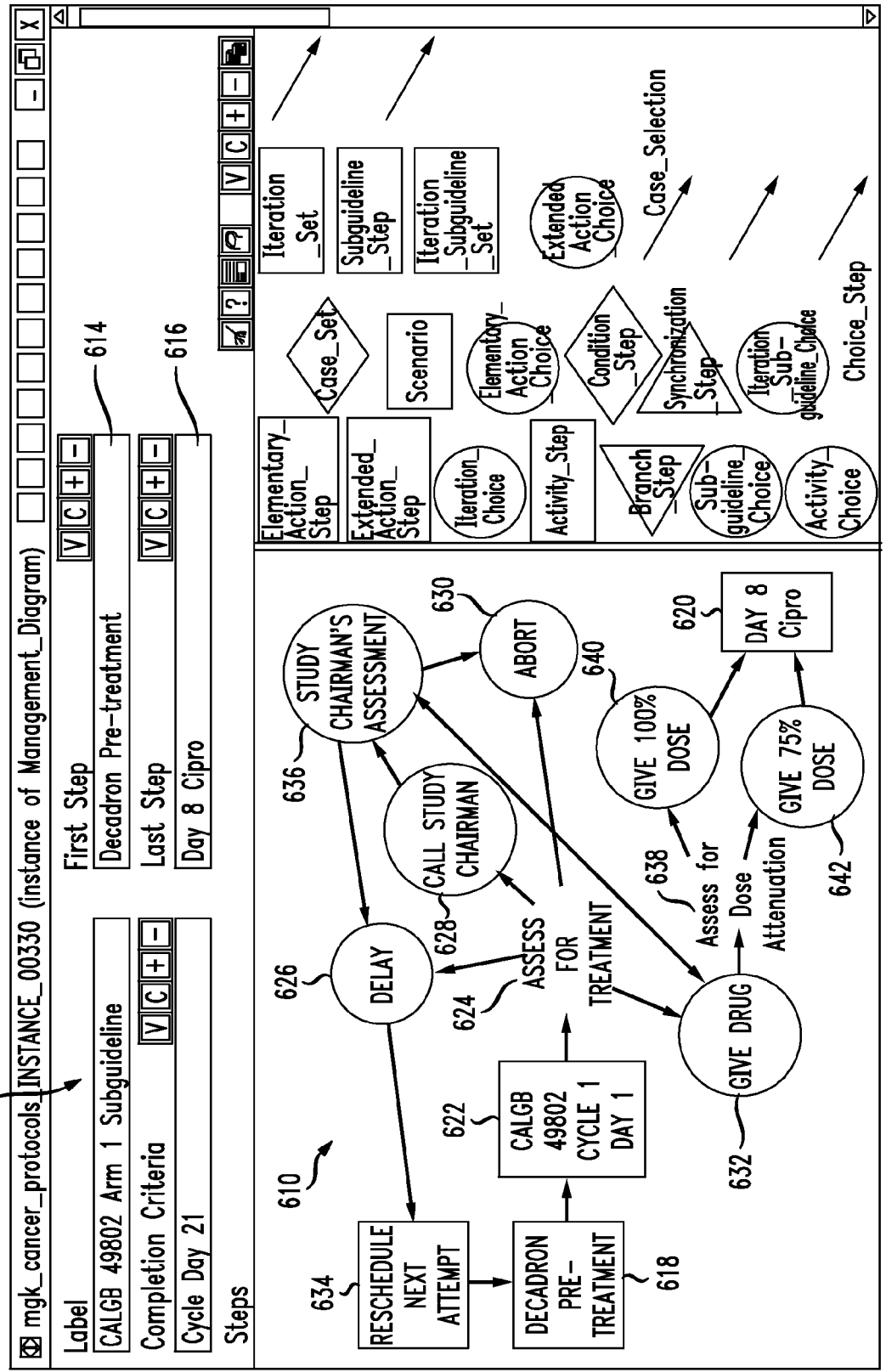

FIG. 6 is a detail of the "CALGB 49802 Arm 1" sub-guideline 332 (FIG. 3). As in FIG. 4, FIG. 6 includes a sub-graph (graph 610) and some additional information fields 612. The additional information fields 612 include, among other things, an indication 614 of the first step 618 in the graph, and an indication 616 of the last step 620 of the graph.

Referring to graph 610, the arm 1 sub-guideline begins with a "Decadron pre-treatment" step object 618. The process continues at a "Cycle 1; Day 1" object 622 followed by a choice_object 624 for "Assess for treatment." The clinician may make one of several choices during step 624 including a step of delaying (choice object 626); a step of calling the study chairman (choice object 628); a step of aborting the current patient (choice object 630); or a step of administering the drug under study (choice object 632). If the clinician chooses to delay (object 626), then the patient continues with a "Reschedule next attempt" step 634, followed by another "Decadron pre-treatment" step 618 at a future visit. If in step 624 the clinician chooses to call the study chairman (object 628), then workflow proceeds to choose_step object 636, in which the study chair makes an assessment. The study chair can choose either the delay object 626, the "Give Drug" object 632, or the Abort object 630.

If either the clinician (in object 624) or the study chair (in object 636) chooses to proceed with the "Give Drug" object 632, then workflow proceeds to choice_step object 638 at which the clinician assesses the patient for dose attenuation. In this step, the clinician may choose to give 100% dose (choice object 640) or to give 75% dose (choice object 642). In either case, after dosing, the clinician then performs "Day 8 Cipro" step object 620. That is, on the $8^{th}$ day, the patient begins a course of Ciprofloxacin (an antibiotic).

Without describing the objects in the graph 610 individually, it will be understood that many of these objects either are themselves specific tasks, or contain task lists which are associated with the particular step, visit or decision represented by the object.

Figure 7:
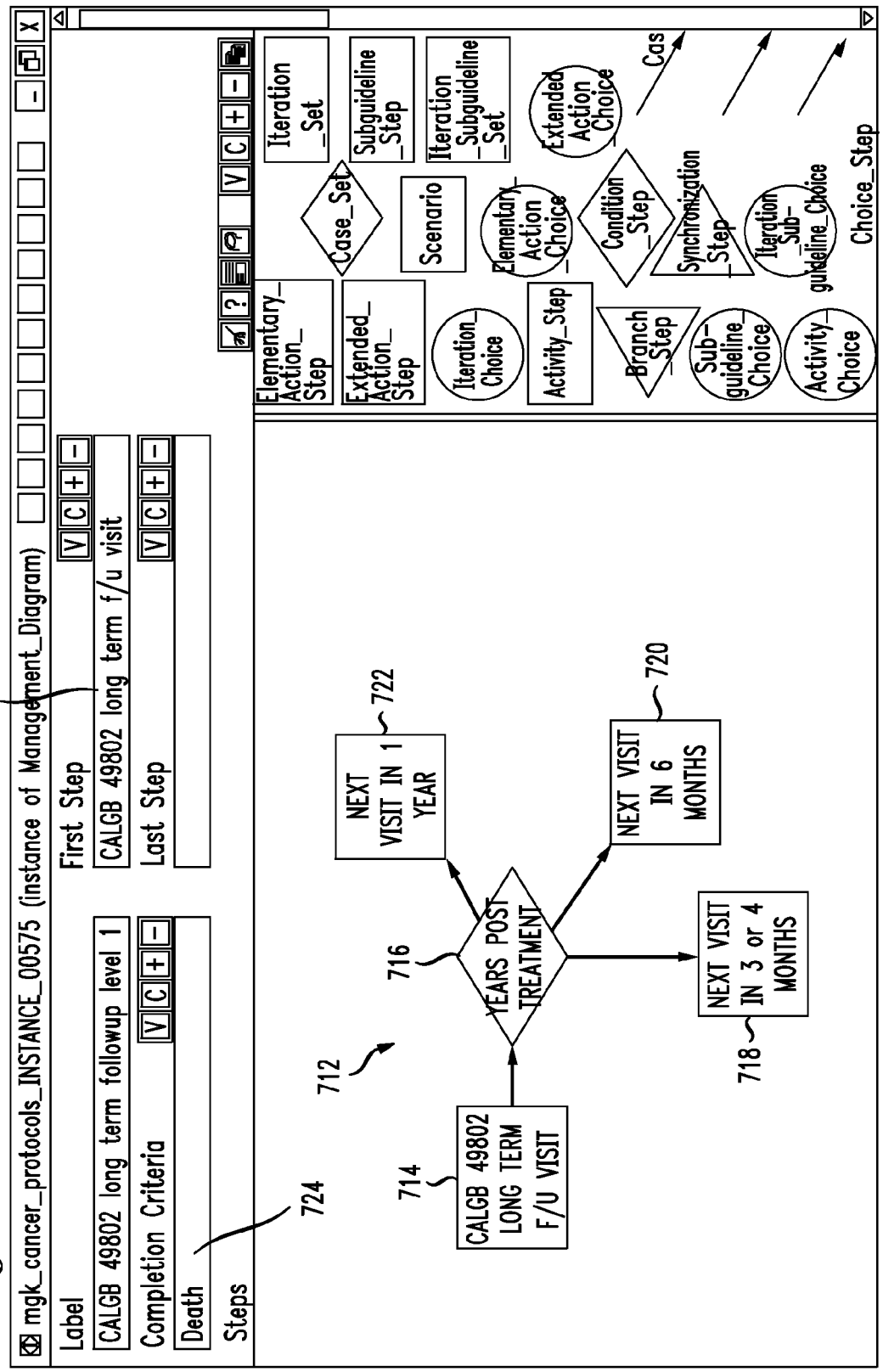

FIG. 7 is a detail of the long term follow-up object 332 (FIG. 3). As mentioned in field 710, the first step in the sub-graph 712 of this object is a long term follow-up visit scenario visit object 714. That is, the sub-guideline illustrated in graph 712 is executed on each of the patient's long-term follow-up visits. As indicated in field 724, the long term follow-up step 332 (FIG. 3) continues until the patient dies.

Object 716 is a case object which is dependent upon the patient's number of years post-treatment. If the patient is 1-3 years post-treatment, then the patient proceeds to step object 718, which among other things, schedules the next visit in 3-4 months. If the patient is 4-5 years post-treatment, then the patient proceeds to step object 720, which among other things, schedules the next patient visit in 6 months. If the patient is more than 5 years post-treatment, then the patient proceeds to step object 722, which among other things, schedules the next visit in one year. Accordingly, it can be seen that in the sub-guideline 712, different tasks are performed if the patient is less than 3 years out from therapy, 4-5 out from therapy, or more than 5 years out from therapy. Beneath each of the step objects 718, 720 and 722 are additional workflow tasks that the clinician is required to perform at the current visit.

Figure 8:
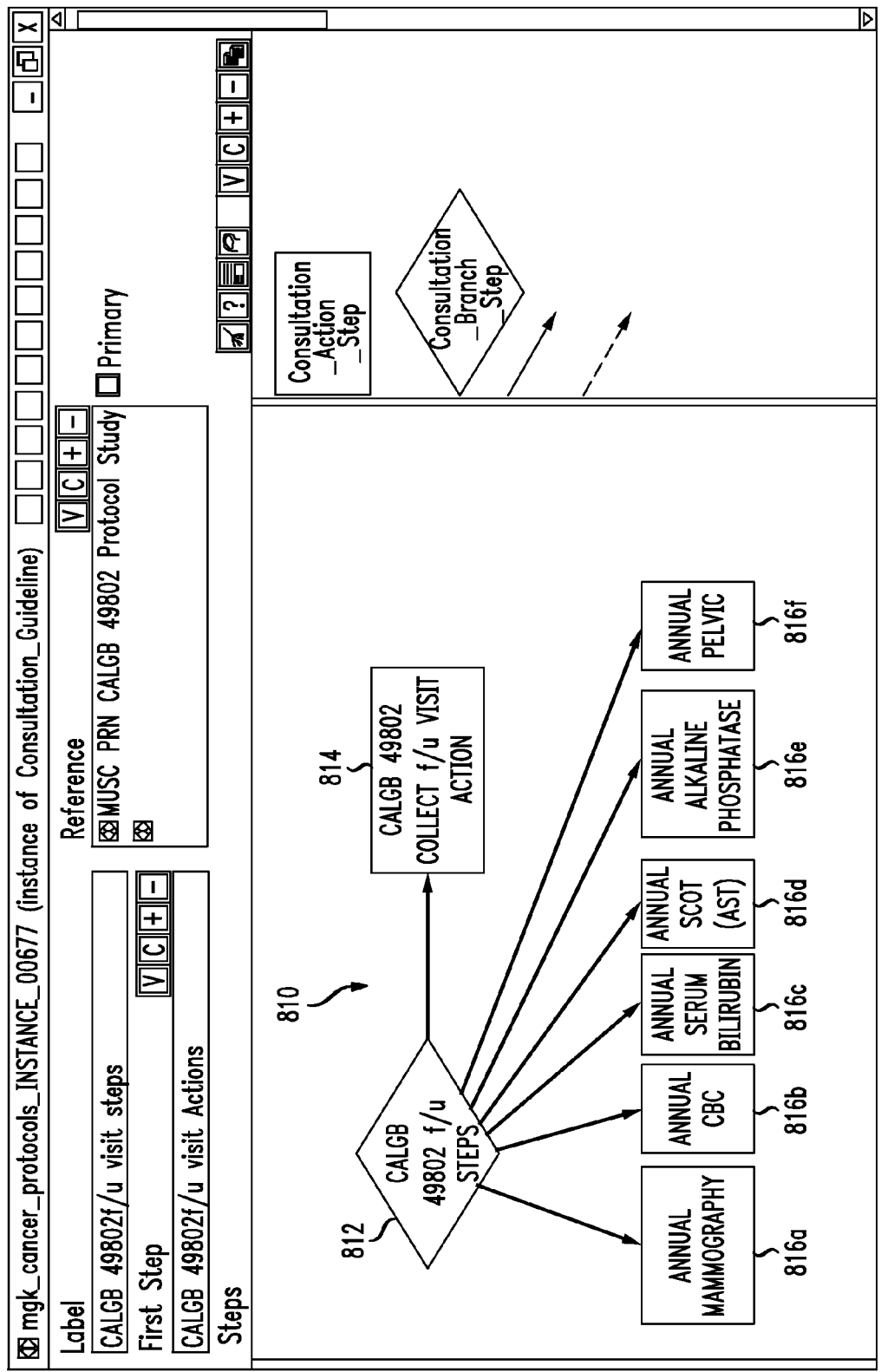

FIG. 8 is an example detail of one of the objects 718, 720 or 722 (FIG. 7). It includes a graph 810 which begins with a CALGB 49802 f/u visit steps" consultation_branch object 812, followed by seven elementary action objects 814 and 816*a-f*(collectively 816). Each of the consultation_action objects 814 and 816 includes a number of workflow tasks not shown in the figures. It can be seen from the names of the objects, however, that the workflow tasks under object 814 are to be performed at every follow-up visit, whereas the workflow tasks under objects 816 are to be performed only annually.

As mentioned, the iCP facilitates integration of all the tools in the overall system of FIG. 1. Integration and especially consistency of language, is facilitated also by the use of CMT 112 (FIG. 1). As mentioned, a CMT provides for a consistent set of concepts, terms, and attributes which allow different tools to "understand" the same structures. CMT concepts include treatments, visits, and laboratory tests, for example. CMT terms include cytoxan, neutropenia, and WBC counts, for example. CMT attributes specify, for example, that cytoxan is a drug which has a dosage and can cause specific side effects, neutropenia is a clinical state described by a series of low white blood cell counts which occur together over a short period of time, and WBC counts are blood test results which have a certain range and are a measurement whose validity persists for only a few days. Embodiments described herein use CMT to describe patient eligibility criteria (both preliminary eligibility criteria and further eligibility criteria), and also to describe the individual workflow tasks required of the clinician according to the protocol schema represented in the iCP. In one embodiment, the use of CMT is optional, whereas in another embodiment, the use of CMT is enforced. CMT is used in embodiments described herein also to describe patient medical status information that the clinician obtains and records. No existing clinical trials tool makes use of CMT as described herein.

Returning to FIG. 1, in step 114, the protocol designer uses the authoring tool to encode the eligibility criteria and the protocol schema for the clinical trial being designed. For the protocol schema, the authoring tool creates a graphical tool, called a knowledge acquisition (KA) tool (also considered herein to be part of the protocol authoring tool) that is used by protocol authors to enter the specific features of a clinical trial.

Figure 9:
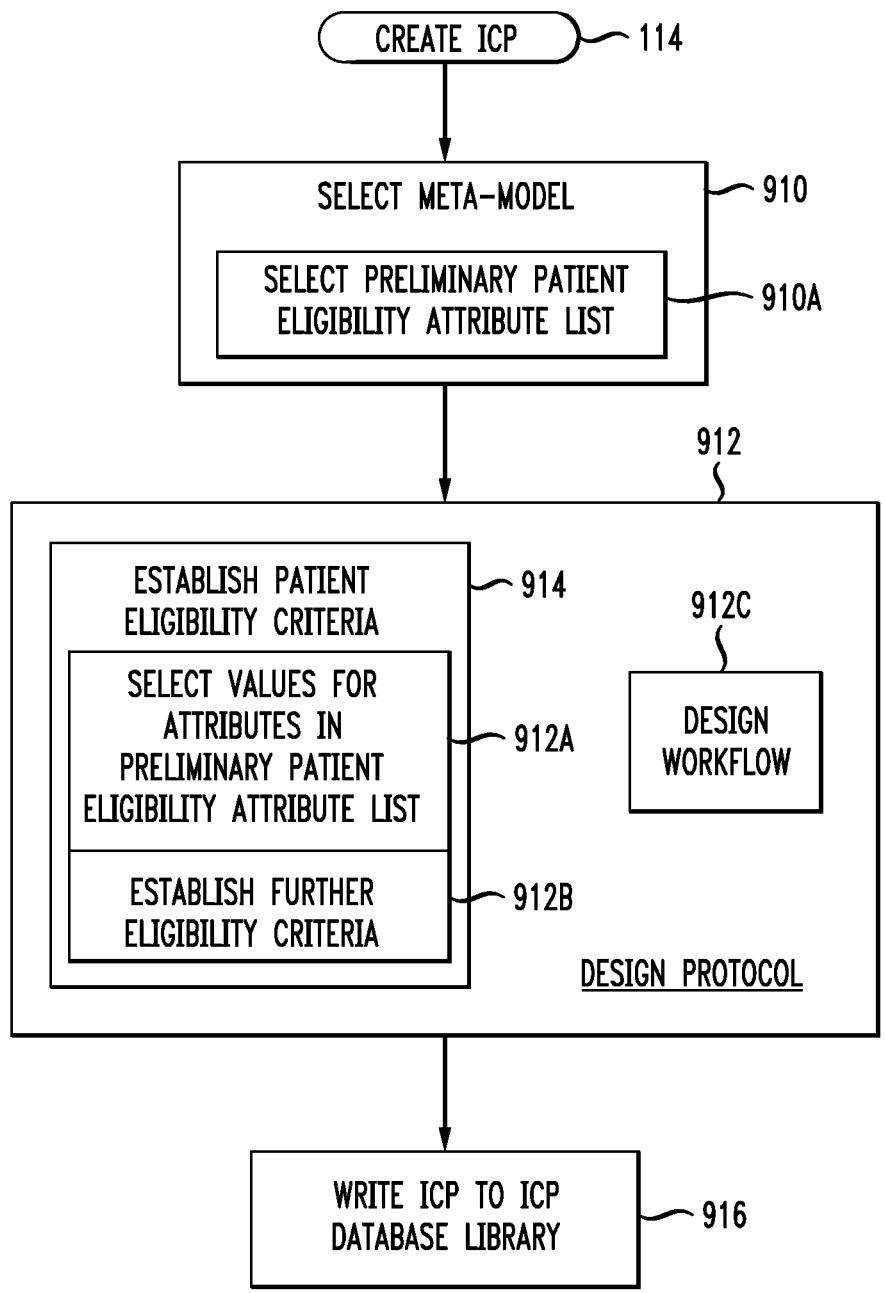
FIG. 9 is a flow chart detail of the step of creating iCPs in FIG. 1.

FIG. 9 is a flow chart detail of the step 114 (FIG. 1). In order to create an iCP, in a step 910, the protocol designer first selects the appropriate meta-model provided by the central authority in step 110. In most but not all cases, if the clinical trial protocol under development involves the testing of a particular treatment against a particular disease, then the step of selecting a meta-model involves merely the selection of the meta-model that has been created for the relevant disease category. In addition, in the embodiment described herein, each meta-model contains only a single list of relevant preliminary patient eligibility attributes and attribute choices. The step 910 of selecting a meta-model therefore also accomplishes a step of selecting one of a plurality of pre-existing lists of preliminary patient eligibility attributes. (Step 910A). As used herein, a list of eligibility attributes can be "defined" by a number of different methods, one of which is by "selecting" the list (or part of the list) from a plurality of previously defined lists of eligibility attributes. This is the method by which the list of preliminary patient eligibility attributes is defined in step 910A.

After the protocol author selects a meta-model, in step 912, the author then proceeds to design the protocol. The step 912 is a highly iterative process, and includes a step 912A of selecting values for the individual attributes in the preliminary patient eligibility attributes list; a step 912B of establishing further eligibility criteria for the protocol; and a step 912C of designing the workflow of the protocol. Generally the step 912A of selecting values for attributes in the preliminary patient attribute list will precede step 912B of establishing the further eligibility criteria, and both steps 912A and 912B will precede the step 912C of designing the work flow. However, at any time during the process, the protocol author might go back to a previous one of these steps to revise one or more of the eligibility criteria.

Figure 10:
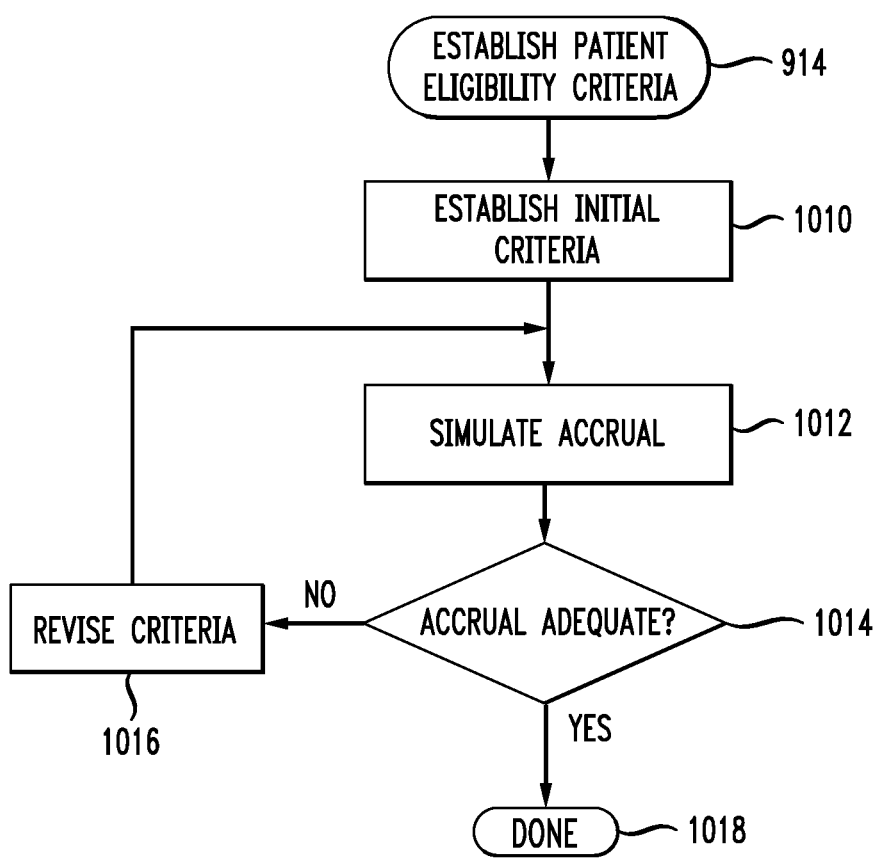
FIG. 10 is a flow chart of an optional method for a protocol author to establish patient eligibility criteria.

FIG. 10 is a flow chart of an advantageous method for the protocol author to establish the patient eligibility criteria. The protocol author is not required to follow the method of FIG. 10, but as will be seen, this method is particularly advantageous. The method of FIG. 10 is shown as a detail of step 914 (FIG. 9), which includes both the steps of selecting values for preliminary patient eligibility attributes and for establishing further eligibility criteria (steps 912A and 912B), rather than as being a detail of step 912A or 912B specifically, because the method of FIG. 10 can be used in either step above, or in both separately, or in both together.

The method of FIG. 10, sometimes referred to herein as an accrual simulation method for establishing patient eligibility criteria, substantially solves the problem mentioned above in which after finalizing a clinical trial protocol, engaging study sites and beginning the enrollment process, it is finally found that the eligibility criteria for the study are too restrictive and that with such criteria it is not possible to enroll sufficient patients in the trial. As mentioned above, these accrual delays are among the most costly and time consuming problems in clinical trials. The method of FIG. 10 addresses this problem by tapping an existing database of patient characteristics (database 116 in FIG. 1) as many times as necessary during the step 912 of designing the protocol, in order to choose eligibility criteria which are likely to enroll sufficient numbers of patients to make the study worthwhile. Generally the effort is to find ways to broaden some or all of the eligibility criteria just enough to satisfy that need, while maintaining sufficient specificity in the study sample to ensure that the patients being treated are sufficiently similar in respect to clinical conditions, co-existing illnesses, and other characteristics which could modify their response to treatment.

Referring to FIG. 10, in step 1010, the protocol author first establishes initial patient eligibility criteria. Depending on which sub-step(s) of step 914 (FIG. 9) is currently being addressed, this could involve selecting values for the attributes in the previously selected patient eligibility attribute list, or establishing further eligibility criteria, or both. In step 1012, an accrual simulation tool runs the current patient eligibility criteria against the accrual simulation database 116 (FIG. 1), and returns the number or percentage of patients in the database who meet the specified criteria. If the database includes a field specifying each patient's location, then the authoring tool can also return an indication of which clinical sites are likely to be most fruitful in enrolling patients.

In one embodiment, the accrual simulation database includes one or more externally provided patient-anonymized electronic medical records databases. In another embodiment, it includes patient-anonymized data collected from various clinical sites which have participated in past studies. In the latter case the patient-anonymized data typically includes data collected by the site during either preliminary eligibility screening, further eligibility screening, or both. Preferably the database includes information about a large number of anonymous patients, including such information as the patient's current stage of several different diseases (including the possibility in each case that the patient does not have the disease); what type of prior chemotherapy the patient has undergone, if any; what type of prior radiation therapy the patient has undergone; whether the patient has undergone surgery; whether the patient has had prior hormonal therapy; metastases; and the presence of cancer in local lymph nodes. Not all fields will contain data for all patients. Preferably, the fields and values in the accrual simulation database 116 are defined according to the same CMT 112 used in the protocol meta-models and preliminary and further eligibility criteria. Such consistency of data greatly facilitates automation of the accrual simulation step 1012. Note that since the patients included in the accrual simulation database may be different from and may not accurately represent the universe of patients from which the various clinical sites executing the study will draw, some statistical correction of the numbers returned by the accrual simulation tool may be required to more accurately predict accrual.

After accrual is simulated with the patient eligibility criteria established initially in step 1010, then in step 1014, the protocol author decides whether accrual under those conditions will be adequate for the purposes of the study. If not, then in step 1016, the protocol author revises the patient eligibility criteria, again either the values in the preliminary patient eligibility criteria list or in the further eligibility criteria or both, and loops back to try the accrual simulation step 1012 again. The process repeats iteratively until in step 1014 the protocol author is satisfied with the accrual rate, at which point the step of establishing patient eligibility criteria 914 is done (step 1018).

In an alternative implementation, the accrual simulation step 1012 is implemented not by querying a preexisting database, but rather by polling clinical sites with the then-current eligibility criteria. Such polling can take place electronically, such as via the Internet. Each site participating in the polling responds by completing a return form, either manually or by automatically querying a local database which indicates the number of patients that the site believes it can accrue who satisfy the indicated criteria. The completed forms are transmitted back to the authoring system, which then makes them available to the protocol author for review. The authoring system makes them available either in raw form, or compiled by clinical site or by other grouping, or merely as a single total. The process then continues with the remainder of the flowchart of FIG. 10.

Returning to FIG. 9, both of the steps 912A and 912B preferably take advantage of concepts, terms and attributes already described in the CMT 112 (FIG. 1). The author may use a CMT browser for this purpose, which can either be built into the authoring tool, or a separate application from which the author may cut and paste into the authoring tool. In addition to the literal concept, terms and attributes entries, the CMT 112 preferable also contains "screen questions", which are more descriptive than the actual entries names themselves, and which help both the protocol author and subsequent users of protocol to interpret each entry consistently.

The step 912C of designing the workflow, results in a graph like those shown in FIGS. 3, 4, 6, 7 and 8 described above. As noted above, the authoring tool allows the protocol author to define not only patient management tasks, but also data management tasks. Such data management tasks can include such items as obtaining informed consent, completing forms regarding patient visits that have taken place, entering workflow progress data (e.g. confirmation that each patient management task identified for a particular visit was in fact performed; and which arm of a branch the patient has taken), and patient medical status information (e.g., patient assessment observations). In addition, preferably the concepts, terms and attributes used in the workflow graph make reference to entries in the CMT database 112. Even more preferably, as in the patient eligibility criteria, the authoring tool enforces reference to a CMT for all concepts, terms and attributes used in the workflow tasks. Again, a CMT browser may be used.

The result of step 912 is an iCP database, such as the one described above with respect to FIGS. 2-8. As can be seen, the iCP contains both eligibility criteria and workflow tasks organized as a graph. The workflow tasks include both patient management tasks and data management tasks, and either type can be positioned on the graph for execution either pre- or post-enrollment.

In step 916, the iCP is written to an iCP database library 118 (FIG. 1), which can be maintained by the central authority. The iCP database library 118 is essentially a database of iCP databases, and includes a series of pointers to each of the individual iCP databases. In an embodiment, the iCP database library also includes appropriate entries to support access restrictions on the various iCP databases, so that access may be given to certain inquirers and not others.

For example, while certain clinical trial protocols are typically publicly available, such as those sponsored by public interest institutions, others, such as those funded by pharmaceutical companies, usually need to be maintained in strict confidence. Those which do not require confidentiality might have no access restrictions other than subscription or membership in the central authority which maintains the iCP library 118, whereas those that do require confidentiality are accessible only by the sponsor itself and by specific clinical sites and SMOs who have signed confidentiality agreements with the sponsor. In an embodiment, the iCP database library 118 includes an access control list for each iCP database, which lists which users (including kinds of users) are allowed access to that database, and optionally what kind of access is permitted for each user (e.g., read/write access, or read access but not write access). The sponsor of each iCP is the only entity that can modify the access control list for the iCP.

Because the process of designing a clinical trial protocol can be extremely complex, usually requiring extensive medical and clinical knowledge, in one aspect of the invention the task is facilitated by allowing subprotocol components to be stored in a library after they are created, and re-used later in other protocols. Subprotocol components can themselves include subprotocol subcomponents which are themselves considered herein to be subprotocol components. In the object-oriented embodiments described above with respect to FIGS. 2-8 and 11-25, the subprotocol components can be any object in an iCP, and subcomponents of such subprotocol components can be any sub-objects of such objects. Referring to FIG. 1, the subprotocol components are stored in a re-usable iCP component library 130, and they are drawn upon as needed by protocol designers in step 114, as well as written to by protocol designers (or sponsors) after an iCP or a portion of an iCP is complete.

In an embodiment, access to the subprotocol components in the re-usable iCP component library 130 is controlled in the same manner as is access to the iCP databases in iCP database library 118. This can be accomplished in various different ways in different embodiments. In one embodiment, the sponsor writes its subprotocol components into the library 130 with whatever granularity is desired. Each such component has associated therewith its own independent access control list, so access to the subprotocol components in the library 130 is controlled with the same granularity that the sponsor used in writing the components into the library 130. In another embodiment, access control lists are applied hierarchically within a subprotocol component, permitting the granularity of access control to be finer than the granularity of objects written into the library 130 by the sponsor. In yet another embodiment the re-usable iCP component library 130 is physically the same as the iCP database library 118, and access control lists are associated with subprotocol components as well as with entire iCP databases.

In step 120, the central authority "distributes" the iCPs from the iCP database library 118 to clinical sites which are authorized to receive them. Authorization typically involves the site being part of the central authority's network of clinical sites, and also authorization by the sponsor of each study. In one embodiment, "distribution" involves merely making the appropriate iCP databases available to the appropriate clinical sites. In another embodiment, "distribution" involves downloading the appropriate iCP databases from the iCP database library 118, into a site-local database of authorized iCPs. In yet another embodiment, the entire library 118 is downloaded to all of the member clinical sites, but keys are provided to each site only for the protocols for which that site is authorized access. Preferably, the central authority maintains the iCP databases only on the central server and makes them available using a central application service provider (ASP) and thin-client model that supports multiple user devices including work stations, laptop computers and hand held devices. The availability of hand held devices allows the deployment of "intelligent" point of care data capture devices in which all protocol-specific, visit-specific and patient-specific required data elements, and their associated data validation rules, can be automatically created using information contained within the iCP. For example, an iCP can specify that if a patient exhibits evidence of an adverse event, additional data collection elements are required. Intelligent point of care data capture can detect the existence of an adverse event and add new required data elements to completely describe the event.

In step 122, the individual clinical sites conduct clinical trials in accordance with one or more iCPs. The clinical site uses either a single software tool or a collection of different software tools to perform a number of different functions in this process, all driven by the iCP database. In one embodiment, in which Protégé was used as a clinical trials protocol authoring tool, a related set of "middleware" components similar to the EON execution engine originally created by Stanford University's Section on Medical Informatics, can be used to create appropriate user applications and tools which understand and which in a sense "execute" the iCP data structure. EON and its relationship to Protégé are described in the above-incorporated SMI Report Number SMI-1999-0801, and also in the following two publications, both incorporated by reference herein: Musen, et. al., "EON: A Component-Based Approach to Automation of Protocol-Directed Therapy, SMI Report No. SMI-96-0606, JAMIA 3:367-388 (1996); and Musen, "Domain Ontologies in Software Engineering: Use of Protege with the EON Architecture," Methods of Information in Medicine 37: 540-550, SMI Report No. SMI-97-0657 (1998).

These middleware components support the development of domain-independent problem-solving methods (PSMs), which are domain-independent procedures that automate tasks to be solved. For example, the software which guides clinical trial procedures at the clinical site uses an eligibility-determination PSM to evaluate whether a particular patient is eligible for one or more protocols. The PSM is domain-independent, meaning that the same software component can be used for oncology trials or diabetes trials, and for any patient. All that changes between different trials is the protocol description, represented in the iCP. This approach is far more robust and scalable than creating a custom rule-based system for each trial, as was done in the prior art, since the same tested components can be reused over and again from trial to trial. In addition to the eligibility determination PSM, there is a therapy-planning PSM that directs therapy based on the protocol and patient data, and the accrual simulation PSM described elsewhere herein, among others.

Because of the ability to support domain-independent PSMs, the iCPs of the embodiments described herein enable automation of the entire trials process from protocol authoring to database lock. For example, the iCP is used to create multiple trial management tools, including electronic case report forms, data validation logic, trial performance metrics, patient diaries and document management reports. The iCP data structures can be used by multiple tools to ensure that the tool performs in strict compliance with the clinical protocol requirements. For example, the accrual simulation tool described above with respect to FIG. 10 is implemented as a domain-independent PSM. Similarly, an embodiment can also include a PSM that clinical sites can use to simulate their own accrual in advance of signing on to perform a given clinical trial. A single PSM is used to simulate accrual into a variety of studies, because the patient eligibility criteria are all identified in a predetermined format in the iCP for each study. Another PSM helps clinical sites identify likely patients for a given clinical trial. Yet another PSM guides clinicians through the visit-specific workflow tasks for each given patient as required by the protocol. The behavior of all these tools is guaranteed to be consistent with the protocol even as it evolves and changes because they all use the same iCP. The tools can also be incorporated into a library that can be re-used for the next relevant trial, thus permitting knowledge to be transferred across trials rather than being re-invented each time.

Figure 26:
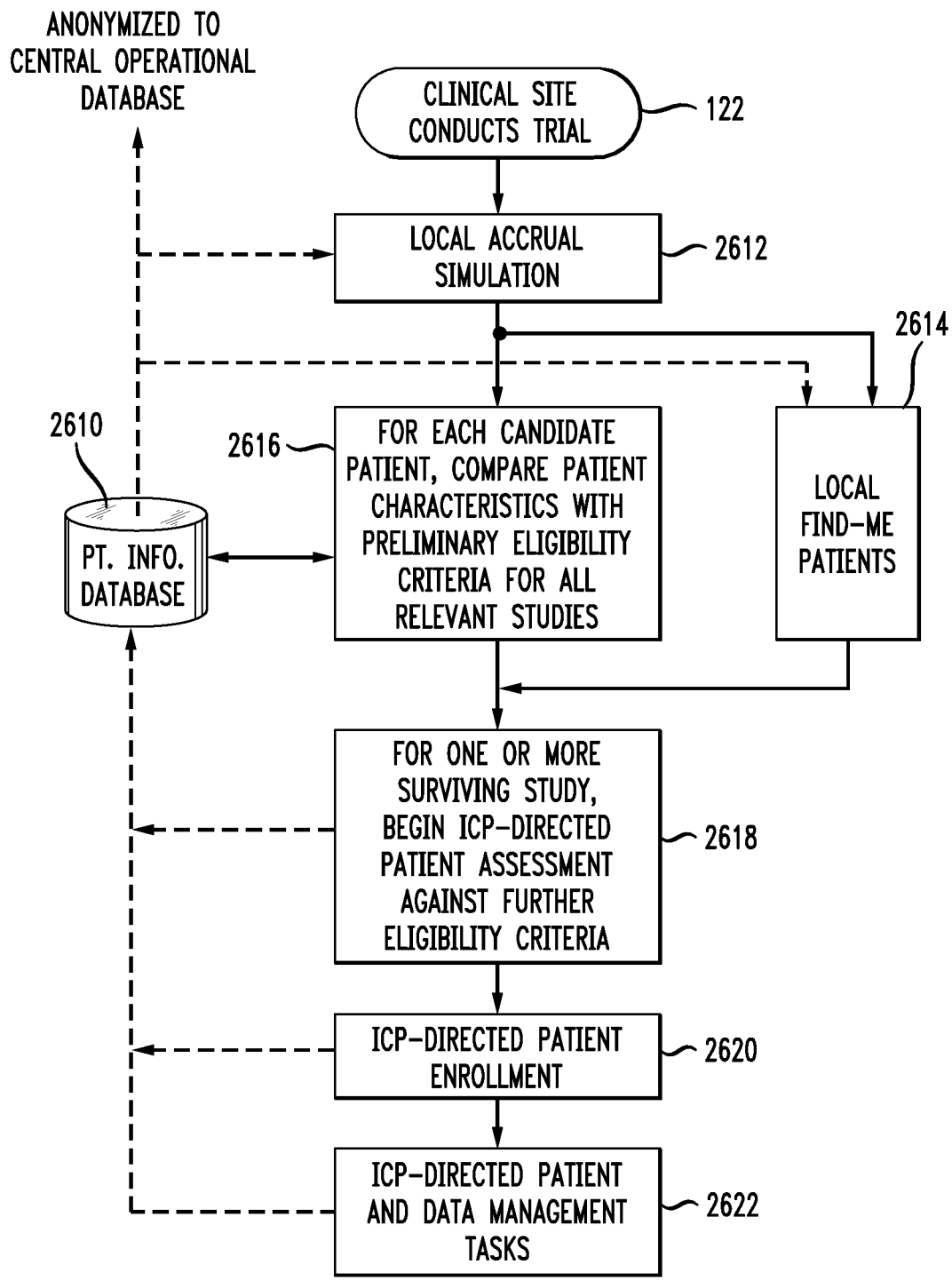
FIG. 26 is a flow chart detail of step 122 (FIG. 1).

FIG. 26 is a flow chart detail of step 122 (FIG. 1). The steps in FIG. 1 typically use or contribute to a site-private patient information database 2610, which contains a number of different kinds of patient information. Because this information is maintained in conjunction with the identity of the patient, these databases 2610 are typically confidential to the clinical site or SMO, and not made available to anyone else, including study sponsors and the central authority. In one embodiment, the patient information database 2610 is located physically at the clinical site. In another embodiment, storage of the database 2610 is provided by the central authority as a service to clinical sites. In the latter embodiment, cryptographic or other security measures may be taken to ensure that no entity but the individual clinical site can view any confidential patient information.

As shown in FIG. 1, the central authority also maintains its own "operational" database 124, containing patient-anonymized patient information. The operational database 124 can be separate from the confidential patient information database(s) 2610 on which case a patient anonymized version of the patient information database 2610, or at least portions of database 2610, are transferred periodically for inclusion in an operational database 124 (FIG. 1). Alternatively, the two databases can be integrated together into one, with the central authority being denied access to sensitive patient-confidential information cryptographically.

Referring to FIG. 26, when a particular site is considering signing on to a clinical study for which it is authorized, it can first perform an accrual simulation, based on the data in its own patient information database 2610, to determine whether it is likely to accrue sufficient numbers of patients to make its participation in the study worthwhile (Step 2612). As mentioned, step 2612 is performed by a PSM which references the preliminary eligibility criteria and, in some embodiments, the further eligibility criteria for the candidate study. This PSM queries the site's information database 2610. Preferably the patient information database 2610 includes an indication of which patients are already enrolled in clinical trials, and excludes them from the predicted accrual count reported by the local accrual simulation tool.

After the clinical site has decided to proceed with a study, then it can use either a "Find-Me Patients" tool (step 2614) or a "QuickScreen" tool (step 2616) to identify enrollment candidates. The "Find-Me Patients" tool is either the same or different from the local accrual simulation tool, and it operates to develop a list of patients from its patient information database 2610 who are likely to satisfy the eligibility criteria for a particular protocol. Again, this local "Find-Me Patients" tool makes appropriate queries to the patient information database 2610 for patients who are believed to satisfy the preliminary eligibility criteria for the subject protocol.

The QuickScreen tool, on the other hand, for each candidate patient, compares that patient's characteristics with the preliminary eligibility criteria for all of the studies which are relevant to that clinical site. In one embodiment, this is an automated process driven by the eligibility criteria for all the relevant protocols, and which queries the site's patient information database 2610. In an embodiment, the QuickScreen tool references only those patient characteristics already stored in the patient information database 2610, for which informed consent from the patient was not originally required, or for which the patient previously gave his or her informed consent for a different purpose. Note that the iCPs in the present embodiment do not actually include the preliminary criteria with the iCP. Rather, the preliminary criteria are provided separately by the central authority in a unified "QuickScreen database". In another embodiment, the preliminary eligibility criteria can be either included directly in the iCP or identified by pointer from the iCP. As used herein, a database "identifies" certain information if it contains the information or if it points to the information, whether or not through one or more levels of indirection.

The studies that the site includes in the QuickScreen step 2616 for a given candidate patient might be all studies for which the site has authorization. Alternatively, the list of candidate studies can be limited to a particular disease area, and/or by the patient's own stated preferences, and/or by other study selection criteria applied by the site. If the QuickScreen step 2616 involves manual entry of newly obtained patient data, then preferably such data is added to the patient information database 2610.

If the candidate patient is determined to satisfy the preliminary eligibility criteria for one or more clinical trials, in step 2616, then in step 2618, the clinical site evaluates the candidate patient's medical characteristics against the further eligibility criteria for one or more of the surviving studies. This step can be performed either serially, ruling out each study before evaluating the patient against the further eligibility criteria of the next study, or partially or entirely in parallel. Preferably the step 2618 for each given study is managed by the workflow management PSM, making reference to the iCP for the given study. The iCP may direct certain patient assessment tasks which are relevant to the further eligibility criteria of the particular study. It also directs the data management tasks which are appropriate so that clinical site personnel enter the patient assessment results into the system for comparison against the further eligibility criteria. Furthermore, as described in more detail elsewhere herein, the iCP can further direct the obtaining of informed consent either at the beginning of the further eligibility evaluation step 2618, or at an appropriate time in the middle when informed consent is required before proceeding. Moreover, where possible, all data entered into the system during step 2618 is recorded in the clinical site's patient information database 2610.

After step 2618, if the patient is still eligible for one or more clinical trials, then in step 2620, the workflow management tool directs and manages the process of enrolling the patient in one of the trials. The fact of enrollment is recorded in the patient information database 2610. In step 2622, the workflow management tool, governed by the iCP database, directs all of the workflow task required at each patient visit in order to ensure compliance with the protocol. As mentioned, in accordance with the protocol, information about the patient's progress through the workflow tasks is written into the patient information database 2610, as is certain additional data called for in the data management tasks of the protocol. In one embodiment, the workflow management tool records performance/non-performance of tasks on a per patient, per visit basis. An another embodiment, more detailed patient progress information is recorded.

Returning to FIG. 1, as can be seen, patient-anonymized medical information as well as workflow progress information is uploaded from the patient information databases 2610 at each of the clinical sites in the network, to a central operational database 124. In various embodiments, some or all of this data is uploaded immediately as created, and/or on a periodic basis. The clinical study sponsors have access to the data in order to permit real time or near-real-time (depending on upload frequency) monitoring of the progress of their studies (Step 126), and the central authority also analyzes the data in the operational database 124 in order to rate the performance of each site against clinical site performance metrics (Step 128).

Such performance metrics include a site's accrual performance (actual vs. expected accrual rates), and the site's ability to deliver timely, accurate information as trials progress. The latter metrics can include such measurements as the time to complete tasks, the time from visit to entered CRF, the time from visit to closed CRF, the time from last visit to closed patient, and the time from last patient last visit to closed study. Prior art systems exist for collecting site performance data, but these systems have captured only very narrow metrics such as completion of case report forms, and the number of audits that have been conducted on the site. The prior art systems are also entirely paper-based. Most importantly, the prior art systems evaluate site performance only for a single specific study; they do not accumulate performance metrics across multiple studies at a given clinical site. In the embodiment described herein, however, the central authority gathers performance data electronically over the course of more than one study being conducted at each participating clinical site. In step 128 the central authority evaluates each site's performance against performance metrics, and these evaluations are based on each site's proven and documented past performance, typically over multiple studies conducted. Preferably, the central authority makes its site performance evaluations available to sponsors such that the best sites can be chosen for conducting clinical trials.

Study sponsors also have access to the data in the operational database 124 in order to identify promising clinical sites at which a particular new study might be conducted. For this purpose, the patient information that has been uploaded to the operational database 124 includes an indication of the clinical site at which the data was collected. The sponsor then executes a "Find-Me-Sites" PSM which queries the operational database 124 in accordance with the iCP or preliminary eligibility criteria applicable to the new protocol, and the PSM returns the number or percentage of patients in the database from each site who satisfy or might satisfy the eligibility criteria.

As used herein, a given event or value is "responsive" to a predecessor event or value if the predecessor event or value influenced the given event or value. If there is an intervening step or time period, the given event or value can still be "responsive" to the predecessor event or value. If the intervening step combines more than one event or value, the output of the step is considered "responsive" to each of the event or value inputs. If the given event or value is the same as the predecessor event or value, this is merely a degenerate case in which the given event or value is still considered to be "responsive" to the predecessor event or value. "Dependency" of a given event or value upon another event or value is defined similarly.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. In particular, and without limitation, any and all variations described, suggested or incorporated by reference in the Background section of this patent application are specifically incorporated by reference into the description herein of embodiments of the invention. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A method for designing a clinical protocol, the method comprising:
creating a plurality of protocol meta-models using a computing device, each of said plurality of protocol meta-models includes at least one list relevant to a designated disease, said at least one list contains a set of patient eligibility criteria and a set of workflow actions, each of said set of patient eligibility criteria includes an attribute associated with the designated disease and an assigned range of values for said attribute to designate if that said patient eligibility criteria is satisfied;
selecting at least one protocol meta-model of said plurality of protocol meta-models using the computing device; and
generating an intelligent clinical protocol database via said computing device using an authoring tool that encodes one or more of said set of patient eligibility criteria and a protocol schema associated with the selected at least one protocol meta-model and that facilitates entry of one or more of said set of workflow actions into the intelligent clinical protocol database.

2. The method of claim 1, wherein said at least one list is represented by a table, said table including one or more categories selected from the group having a disease type, a disease stage, and one or more treatment options.

3. The method of claim 1, wherein said intelligent clinical protocol database is configured to encode significant aspects of the clinical protocol.

4. The method of claim 1, wherein a set of controlled medical terminologies is used when said plurality of protocol meta-models and said intelligent clinical protocol database are created to provide for consistency in the clinical protocol.

5. The method of claim 1, wherein said authoring tool creates a knowledge acquisition tool to add specific features to the intelligent clinical protocol database.

6. The method of claim 1, further comprising an accrual database accessible based on user access controls.

7. The method of claim 1, wherein said plurality of protocol meta-models is distributed by a central authority.

8. The method of claim 1, wherein the clinical protocol is conducted at clinical sites in accordance with the intelligent clinical protocol database.

9. The method of claim 1, wherein the intelligent clinical protocol database is saved in an intelligent clinical protocol database library.

10. The method of claim 1, wherein the intelligent clinical protocol database is saved in a computer readable medium.

11. The method of claim 1, wherein the intelligent clinical protocol database is made available to one or more authorized clinical sites.

12. At least one non-transitory computer readable medium for collectively carrying:
- a plurality of protocol meta-models, each of said plurality of protocol meta-models includes a list relevant to a designated disease, said list contains a set of patient eligibility criteria and a set of workflow actions, each of said set of patient eligibility criteria includes an attribute associated with the designated disease and an assigned range of values for said attribute to designate if that said patient eligibility criteria is satisfied; and
- an authoring tool to generate an intelligent clinical protocol database, said authoring tool encoding a set of patient eligibility criteria and a protocol schema associated with a selected protocol meta-model into the intelligent clinical protocol database and facilitating entry of specific features of a clinical protocol into the intelligent clinical protocol database;
- wherein said intelligent clinical protocol database is generated by:
  - selecting the protocol meta-model from said plurality of protocol meta-models, including selection of preliminary patient eligibility criteria and workflow actions;
  - selecting values for individual attributes in said preliminary patient eligibility criteria;
  - establishing eligibility criteria based on said values selected; and
  - facilitating entry of a workflow based on said workflow actions selected.

13. The medium of claim 12, wherein said intelligent clinical protocol database is revised by changing one or more individual attributes in said preliminary patient eligibility criteria.

14. The medium of claim 12, wherein said intelligent clinical protocol database is revised by changing one or more eligibility criteria.

15. An article comprising a machine-readable medium storing machine-readable instructions that, when applied to a machine, cause the machine to:
- create a plurality of protocol meta-models using a computing device, each of said plurality of protocol meta-models includes at least one list relevant to a designated disease, said at least one list contains a set of patient eligibility criteria and a set of workflow actions, each of said set of patient eligibility criteria includes an attribute associated with the designated disease and an assigned range of values for said attribute to designate if that said patient eligibility criteria is satisfied;
- select at least one protocol meta-model of said plurality of protocol meta-models from a using the computing device; and
- generate an intelligent clinical protocol database via said computing device using an authoring tool that encodes one or more of said set of patient eligibility criteria and a protocol schema associated with the selected at least one protocol meta-model and that facilitates entry of one or more of said set of workflow actions into the intelligent clinical protocol database.

16. The article of claim 15, wherein the intelligent clinical protocol database is made available to one or more authorized clinical sites.

17. The article of claim 15, wherein said machine graphically displays said intelligent clinical protocol database.

* * * * *